US011026865B2

(12) United States Patent
Hart et al.

(10) Patent No.: US 11,026,865 B2
(45) Date of Patent: Jun. 8, 2021

(54) ACCELERATED DRYING OF SOFT CAPSULES IN A CONTROLLED ENVIRONMENT

(71) Applicant: R.P. Scherer Technologies, LLC, Las Vegas, NV (US)

(72) Inventors: Norton Richard Hart, Clearwater, FL (US); Lester David Fulper, Clearwater, FL (US)

(73) Assignee: R.P. Scherer Technologies, LLC, Las Vegas, NV (US)

( * ) Notice: Subject to any disclaimer, the term of this patent is extended or adjusted under 35 U.S.C. 154(b) by 105 days.

(21) Appl. No.: 16/467,436

(22) PCT Filed: Dec. 8, 2017

(86) PCT No.: PCT/US2017/065290
§ 371 (c)(1),
(2) Date: Jun. 6, 2019

(87) PCT Pub. No.: WO2018/107019
PCT Pub. Date: Jun. 14, 2018

(65) Prior Publication Data
US 2020/0069525 A1 Mar. 5, 2020

Related U.S. Application Data

(60) Provisional application No. 62/431,569, filed on Dec. 8, 2016.

(51) Int. Cl.
*A61J 3/07* (2006.01)
*F26B 21/04* (2006.01)
(Continued)

(52) U.S. Cl.
CPC ............. *A61J 3/077* (2013.01); *F26B 21/004* (2013.01); *F26B 21/04* (2013.01); *F26B 21/08* (2013.01);
(Continued)

(58) Field of Classification Search
CPC . A61J 3/077; A61J 9/4825; F26B 3/02; F26B 5/06; F26B 21/005; F26B 21/004; F26B 21/10; F26B 21/08; F26B 21/12
(Continued)

(56) References Cited

U.S. PATENT DOCUMENTS 1,330,238 A * 2/1920 Carrier .................... F26B 21/06
34/474
5,200,191 A 4/1993 Steele et al.
(Continued)

FOREIGN PATENT DOCUMENTS

CA 3041560 A1 * 6/2018 .............. A61J 3/077
CN 102283779 A 12/2011
(Continued)

OTHER PUBLICATIONS

International Search Report for International Patent Application No. PCT/US2017/065290; dated Apr. 9, 2018.
(Continued)

*Primary Examiner* — Stephen M Gravini
(74) *Attorney, Agent, or Firm* — Mendelsohn Dunleavy, P.C.

(57) ABSTRACT

A method of drying soft capsules including steps of: a) supplying a flow of air to said soft capsules at a velocity of the air across the soft capsules of from about 0.15 m/s to about 13 m/s; b) increasing, over time, a drying temperature to which said soft capsules are exposed while ensuring that the drying temperature remains below a melting temperature of a capsule shell of the soft capsules; c) exposing said soft
(Continued)

capsules to an initial relative humidity of from about 49% RH to about 79% RH; d) decreasing the relative humidity to which the soft capsules are exposed as the capsules dry until an equilibrium relative humidity of the soft capsules reaches a desired relative humidity; and e) exposing the soft capsules from step d) to a temperature of from 20-25° C. Also disclosed is a drying system for carrying out the method.

14 Claims, 12 Drawing Sheets

(51) Int. Cl.
    *F26B 21/08*      (2006.01)
    *F26B 21/10*      (2006.01)
    *F26B 21/12*      (2006.01)
    *F26B 21/00*      (2006.01)
    *A61K 9/48*      (2006.01)
    *F26B 3/02*      (2006.01)

(52) U.S. Cl.
    CPC .............. *F26B 21/10* (2013.01); *F26B 21/12* (2013.01); *A61K 9/4825* (2013.01); *F26B 3/02* (2013.01)

(58) Field of Classification Search
    USPC .......................................................... 34/486
    See application file for complete search history.

(56) References Cited

U.S. PATENT DOCUMENTS

| | | | | |
|---|---|---|---|---|
| 5,724,751 | A * | 3/1998 | Ellingsen | C02F 1/34 34/354 |
| 5,996,247 | A * | 12/1999 | Kuboyama | A23N 12/08 34/370 |
| 7,721,460 | B2 * | 5/2010 | Albers | F24F 3/1417 34/80 |
| 7,762,006 | B2 * | 7/2010 | Kasso | F26B 21/001 34/90 |
| 7,957,842 | B2 | 6/2011 | Boder et al. | |
| 8,256,135 | B2 * | 9/2012 | Hedman | A01M 19/00 34/381 |
| 8,621,764 | B2 | 1/2014 | Puckett | |
| 8,898,927 | B2 * | 12/2014 | Shan | F26B 23/00 34/282 |
| 9,841,234 | B2 * | 12/2017 | Stahl | F26B 3/04 |
| 10,422,579 | B2 * | 9/2019 | Kozlowski | F26B 21/08 |
| 10,590,594 | B2 * | 3/2020 | Berdut-Teruel | F26B 21/04 |
| 2008/0000099 | A1 | 1/2008 | Victorov et al. | |
| 2009/0210094 | A1 | 8/2009 | Boder et al. | |
| 2014/0093606 | A1 | 4/2014 | De Bock et al. | |
| 2020/0069524 | A1 * | 3/2020 | Fulper | F26B 21/12 |
| 2020/0069525 | A1 * | 3/2020 | Hart | F26B 21/10 |
| 2020/0355432 | A1 * | 11/2020 | Yu | F26B 11/0445 |

FOREIGN PATENT DOCUMENTS

| | | | | |
|---|---|---|---|---|
| CN | 104991591 A | 10/2015 | | |
| CN | 105674699 A | 6/2016 | | |
| CN | 105987587 A | 10/2016 | | |
| JP | 2007192464 A | 8/2007 | | |
| JP | 2012006861 A | 1/2012 | | |
| KR | 1020090077304 A | 7/2009 | | |
| KR | 100954481 B1 | 4/2010 | | |
| WO | WO-2018107019 A1 * | 6/2018 | | F26B 21/12 |
| WO | WO-2018107080 A1 * | 6/2018 | | A61J 3/07 |
| WO | WO-2019014722 A1 * | 1/2019 | | A23L 3/54 |

OTHER PUBLICATIONS

ISA Written Opinion for International Patent Application No. PCT/US2017/065290; dated Apr. 9, 2018.
Coppola M., et al. "Phase diagram of gelatin plasticized by water and glycerol." In Macromolecular symposia (vol. 273, No. 1, pp. 56-65). WILEY-VCH Verlag.
First Office Action for corresponding Chinese application No. 201780069164.1; dated May 18, 2020; Machine Translation (15 pages).
Extended European Search Report for corresponding European application No. 17877660.5; dated May 4, 2020 (9 pages).
Fulper, David et al., "Effect of Humidity and Water Content on Water Vapor Transmission through Gelatin Films", American Association of Pharmaceutical Scientists—Annual Meeting, Chicago, Oct. 17, 2012, pp. 1-6.
Examination Report for corresponding Indian application No. 201917019990; dated Jan. 12, 2021 (5 pages).
Second Office Action for corresponding Chinese application No. 201780069164.1; dated Jan. 22, 2021 (20 pages).
Communication pursuant to Article 94(3) for corresponding European application No. 178776605; dated Dec. 21, 2020 (5 pages).

* cited by examiner

ACCELERATED DRYING OF SOFT CAPSULES IN A CONTROLLED ENVIRONMENT

BACKGROUND OF THE INVENTION

1. Field of the Invention

The present invention relates to a method and a drying system that accelerate the drying time of soft capsules in a controlled environment.

2. Description of the Related Technology

In a typical softgel encapsulation process, capsules are conveyed, tumble dried, stacked on trays, and placed in a drying tunnel or drying room in conditions of low humidity and at ambient temperature until the capsules reach a certain specification such as weight loss, hardness, equilibrium relative humidity, or fill moisture. Depending on the formulation of the softgel capsule, the drying time typically ranges from 2 to 10 days. Further, defects, such as sticking or leaking capsules, may occur if capsules are not removed in a timely manner.

Softgel drying has been done at low levels of humidity for a wide range of products, and drying conditions are not necessarily based on the final specification of the particular product. This approach results in inefficient drying and has the potential to over dry capsules, resulting in excessive brittleness and subsequent capsule breakage. Additionally, the use of low levels of humidity may also cause the outside of the gel material to dry faster than the inner parts, which leads to a harder shell material, and creates internal stresses in the capsule. Such internal stresses may reduce the overall robustness of the final product. As such, a reduction in defects and drying cycle time for drying of softgel capsules is needed.

U.S. Pat. No. 8,621,764 discloses a gelatin capsule manufacturing and drying system and process. The drying system and process include a drying structure that is divided into three zones. Each zone includes its own air handler that is capable of heating or cooling the air provided to its respective zone. A single HVAC unit is connected to all of the air handlers. A series of tumble dryers extend through the structure from the first zone to the third zone. Each zone is maintained at different conditions of humidity and temperature. The temperature of each of the zones is controlled using the heater and chillers within the air handling units, and the humidity is varied based on the changes in temperature. The second zone is the warmest, with the highest temperature in this zone being 87° F. The first zone is maintained at the highest relative humidity of all of the zones, with the maximum relative humidity in this zone being 23%. Although the disclosure indicates that a large reduction in drying time is achieved, much of that reduction may be attributable to a reduction in the water content of the starting gelatin.

It is known that increasing the temperature will decrease the drying time of a softgel capsule. However, prior attempts at increasing the temperature above the standard temperatures have resulted in unacceptable defects in the resulting capsules. The defects are created as the softgel cools from the higher temperature. During the cooling process, areas within the gel where the water was removed may be of differing sizes and may contract to different extents, resulting in dimples or dents in the surface of the capsule.

Thus, a system and method that reduces the time for drying softgel capsules is required that produces capsules with the same number, or preferably less defects that the longer drying processes known in the art.

SUMMARY OF THE INVENTION

In a first embodiment, the invention relates to a method of drying soft capsules. The method includes steps of:
 a) supplying a flow of air to said soft capsules at a velocity of the air across the soft capsules of from about 0.15 m/s to about 13 m/s;
 b) increasing, over time, a drying temperature to which said soft capsules are exposed while ensuring that the drying temperature remains below a melting temperature of a capsule shell of the soft capsules;
 c) exposing said soft capsules to an initial relative humidity of from about 49% RH to about 79% RH;
 d) decreasing the relative humidity to which the soft capsules are exposed as the capsules dry until an equilibrium relative humidity of the soft capsules reaches a desired relative humidity; and
 e) exposing the soft capsules from step d) to a temperature of from 20-25° C.

In some embodiments, the method may further include a step of:
 decreasing the velocity of the airflow to which the soft capsules are exposed, as the soft capsules dry.

In each of the foregoing embodiments, the relative humidity may be controlled so that a differential between the relative humidity to which the soft capsules are exposed and the equilibrium relative humidity of the soft capsules is maintained at about 15% dRH to about 35% dRH.

In each of the foregoing embodiments, the soft capsules may be lipophilic. In the foregoing embodiments when the soft capsules are lipophilic, the initial relative humidity may be from about 49% RH to about 79% RH. In the foregoing embodiments when the solfte capsules are lipophilic, a lowest relative humidity to which the soft capsules are exposed may be from about 10% RH to about 24% RH.

In each of the foregoing embodiments, the soft capsules may be hydrophilic. In each of the foregoing embodiments wherein the soft capsules are hydrophilic, the initial relative humidity may be from about 49% RH to about 79% RH and a lowest relative humidity to which the soft capsules are exposed may be from about 23% RH to about 57% RH.

In another embodiment, the invention relates to a drying system for drying soft capsules. The drying system may include:
 at least one dryer;
 a unit in fluid communication with the dryer to provide an airflow to the dryer;
 a humidifier configured to be able to increase the relative humidity within the dryer; and
 a heater configured to be able to increase a temperature of the air in the dryer.

The foregoing drying system may include a recirculation fan located and configured to recirculate a return air stream from the exhaust of the dryer to the unit that provides the airflow to the dryer. In each of the foregoing drying systems the humidifier may include the recirculation fan.

Each of the foregoing drying systems may further include a flow control valve configured to control an amount of the airflow from the unit to the dryer.

Each of the foregoing drying systems may further include a recirculation fan located and configured to recirculate a return air stream from the exhaust of the dryer to the unit that provides the airflow to the dryer, and the flow control valve may be configured such that reducing the amount of airflow from the unit to the dryer increases the relative humidity within the dryer and increasing the amount of airflow from the unit to the dryer decreases the relative humidity within the dryer.

In each of the foregoing drying systems, the heater may be configured to increase the temperature over time according to a temperature ramp based on a melting point of a capsule shell of the soft capsules. In this embodiment, a combination of the flow control valve and the humidifier may be configured to control the relative humidity in the dryer such that the relative humidity in the dryer decreases over time from an initial relative humidity of about 49% RH to about 79% RH to an endpoint relative humidity of about 10% RH to about 24% RH. In the foregoing embodiments, the combination of the flow control valve and the humidifier may be configured to control the relative humidity in the dryer such that the relative humidity in the dryer decreases over time from an initial relative humidity of about 49% RH to about 79% RH to an endpoint relative humidity of about 23% RH and about 57% RH. The relative humidity may be decreased in a manner whereby a differential between the relative humidity in the dryer and the equilibrium relative humidity of the soft capsules is maintained at about 15% dRH to about 35% dRH. The relative humidity may be decreased in a manner whereby a differential between the relative humidity in the dryer and the equilibrium relative humidity of the soft capsules is maintained at about 15% dRH to about 35% dRH.

In yet another embodiment, the invention relates to a method of drying soft capsules. The method includes steps of:
a) supplying a flow of air to said capsules at a velocity of the air across the soft capsules of from about 0.15 m/s to about 13 m/s;
b) increasing, over time, a drying temperature to which said soft capsules are exposed while ensuring that the drying temperature remains below a melting temperature of the capsule shell;
c) maintaining a differential between the relative humidity in the dryer and the equilibrium relative humidity of the soft capsules of about 15% dRH to about 35% dRH until the equilibrium relative humidity of the soft capsules reaches a desired relative humidity; and
d) exposing the soft capsules from step c) to a temperature of from 20-25° C.

DETAILED DESCRIPTION OF THE PREFERRED EMBODIMENT(S)

Figure 1:
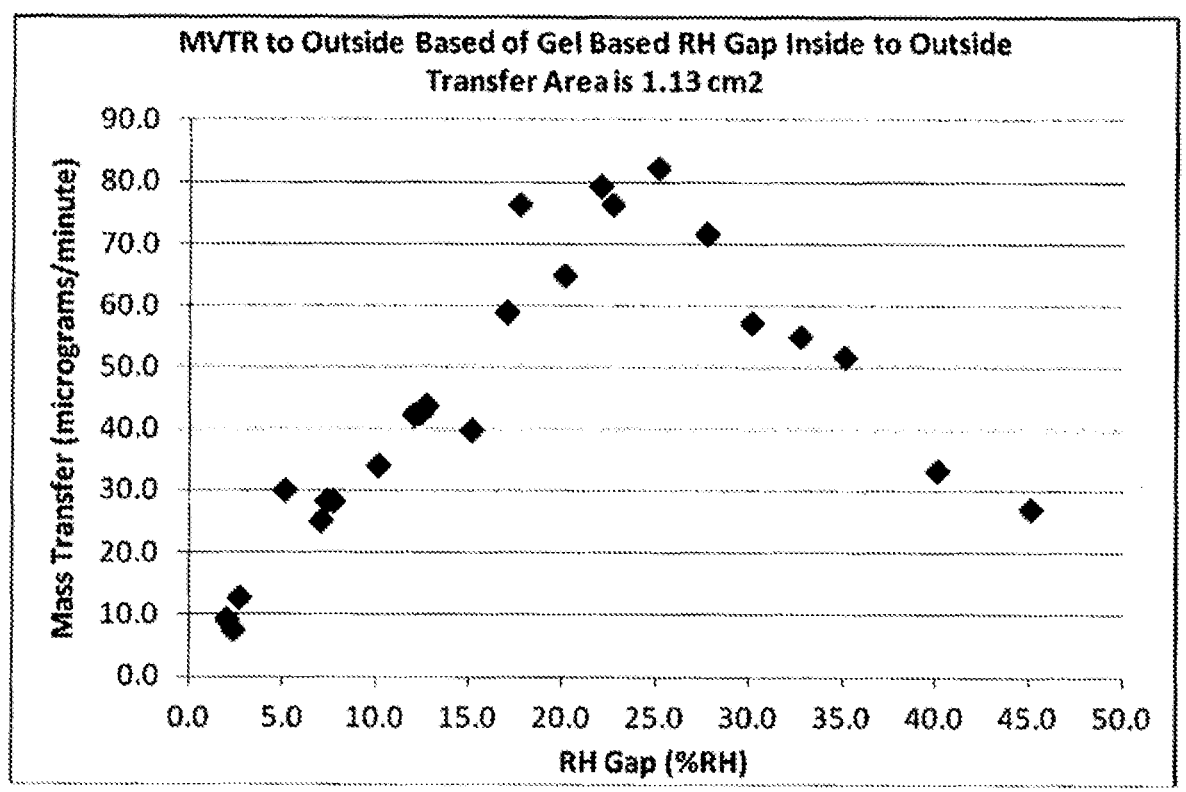
FIG. 1 is a graph showing water flux rate versus a differential between the relative humidity in the drying system and the equilibrium relative humidity of a saturated salt solution through a gelatin film.

For illustrative purposes, the principles of the present invention are described by referencing various exemplary embodiments. Although certain embodiments of the invention are specifically described herein, one of ordinary skill in the art will readily recognize that the same principles are equally applicable to, and can be employed in, other systems and methods. Before explaining the disclosed embodiments of the present invention in detail, it is to be understood that the invention is not limited in its application to the details of any particular embodiment shown. Additionally, the terminology used herein is for the purpose of description and not for limitation. Furthermore, although certain methods are described with reference to steps that are presented herein in a certain order, in many instances, these steps can be performed in any order as may be appreciated by one skilled in the art; the novel method is therefore not limited to the particular arrangement of steps disclosed herein.

It must be noted that as used herein and in the appended claims, the singular forms "a", "an", and "the" include plural references unless the context clearly dictates otherwise. Furthermore, the terms "a" (or "an"), "one or more", and "at least one" can be used interchangeably herein. The terms "comprising", "including", "having" and "constructed from" can also be used interchangeably.

Unless otherwise indicated, all numbers expressing quantities of ingredients, properties such as molecular weight, percent, ratio, reaction conditions, and so forth used in the specification and claims are to be understood as being modified in all instances by the term "about," whether or not the term "about" is present. Accordingly, unless indicated to the contrary, the numerical parameters set forth in the specification and claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

It is to be understood that each component, compound, substituent or parameter disclosed herein is to be interpreted as being disclosed for use alone or in combination with one or more of each and every other component, compound, substituent or parameter disclosed herein.

It is also to be understood that each amount/value or range of amounts/values for each component, compound, substituent or parameter disclosed herein is to be interpreted as also being disclosed in combination with each amount/value or range of amounts/values disclosed for any other component(s), compounds(s), substituent(s) or parameter(s) disclosed herein and that any combination of amounts/values or ranges of amounts/values for two or more component(s), compounds(s), substituent(s) or parameters disclosed herein are thus also disclosed in combination with each other for the purposes of this description.

It is further understood that each lower limit of each range disclosed herein is to be interpreted as disclosed in combination with each upper limit of each range disclosed herein for the same component, compounds, substituent or parameter. Thus, a disclosure of two ranges is to be interpreted as a disclosure of four ranges derived by combining each lower limit of each range with each upper limit of each range. A disclosure of three ranges is to be interpreted as a disclosure of nine ranges derived by combining each lower limit of each range with each upper limit of each range, etc. Furthermore, specific amounts/values of a component, compound, substituent or parameter disclosed in the description or an example is to be interpreted as a disclosure of either a lower or an upper limit of a range and thus can be combined with any other lower or upper limit of a range or specific amount/value for the same component, compound, substituent or parameter disclosed elsewhere in the application to form a range for that component, compound, substituent or parameter.

The present invention relates to a system and method for accelerating the drying of soft capsules by controlling temperature, humidity, and/or velocity of airflow to which the soft capsules are exposed during the drying process. In particular, the diffusion or flux rate of water through a gelatin-containing capsule shell is controlled by controlling the drying environment. More specifically, the relative humidity, temperature and/or airflow in the drying environment is controlled to influence the diffusion or flux rate of water through the gelatin-containing capsule shell.

An increase in drying temperature is known to result in a faster rate of drying. However, as discussed above, there are limits to the reduction in drying time that can be achieved by only increasing the drying temperature since undesirable defects in the soft capsules may result. Thus, in addition to controlling the temperature during the drying process, the velocity of air flowing through the drying environment may also be controlled to provide a further decrease the drying time of the soft capsule while avoiding some of the defects that might otherwise arise from high temperature drying.

Controlling the velocity of the airflow in the drying environment provides some advantages. For example, the evaporation of water, as derived from Fick's Law is given as, $$N_{H2O} = D_{ab} * P/(RTz) * \ln[(P-P_{sat})/(P-P_{wet})]$$

where $N_{H2O}$ is the flux rate of water, $D_{ab}$ is the diffusivity constant through a material, P is the atmospheric pressure, R is the ideal gas constant, T is the ambient temperature, z is the length of stagnant air, $P_{sat}$ is the saturated pressure of water at relative humidity and $P_{wet}$ is the saturated pressure at $T_{wet}$ using a wet bulb thermometer.

Fick's Law indicates that diffusion of water across the capsule shell is directly proportional to the temperature. Thus, at higher temperatures, a higher rate of diffusion can be maintained. In addition, Fick's Law also indicates that the length of stagnant air (z) is proportional to the velocity of airflow. Thus, diffusion of water across the capsule shell is also proportional to the velocity of airflow.

Although temperature is a major driver in drying softgel capsules, when the temperature is increased to above a certain level, the quality of the finished product decreases. Specifically, the capsule shell becomes hardened and thus, when the temperature is reduced upon completion of drying, the volume of the fill shrinks due to the reversal of thermal expansion. The hardened shell is not able to flex with the reduction in fill volume, which results in unacceptable dimples and dents being formed in the shell.

The present system and method includes controlling both the temperature and the relative humidity of the drying system during the drying process. This combination has been found to significantly decrease the drying time of the capsule, as well as significantly reduce or prevent defects in the final product which would otherwise occur due to high drying temperatures.

As the capsules dry, the temperature is increased to maintain a high rate of moisture removal from the capsules via diffusion of water across the capsule shell. The amount of temperature increase is determined based on the melting point of the specific formulation of the capsule shell at specific equilibrium relative humidity's (ERHs). As the temperature increases, the diffusion or flux rate of water across the gelatin-containing capsule shell is accelerated as expected.

In addition, the environmental humidity is also controlled throughout the drying process in order to reduce or prevent formation of defects such as dimples and/or dents upon final cooling of the dried capsule shell. Controlling the humidity may also further increase the drying rate.

The present drying system and process provide a significant reduction in drying time, and produce acceptable dried soft capsules. The resulting soft capsules may also have additional beneficial physical properties that are desired in soft capsules, such as increased robustness.

The article "Phase Diagram of Gelatin Plasticized by Water and Glycerol" by Mara Coppola, et al. of the Thermal Physics Laboratory in Paris, France, and Capsugel in Colmar, France as presented at the Macromol Symposium, 2008, vol. 273, p 56-65, the disclosure of which is hereby incorporated herein by reference, studied gelatin sorption curves at different levels of plasticizers and the corresponding melting-points and glass transition temperatures at different levels of moisture and plasticizer. The effect of gelatin concentration on the melting temperature of films having varying concentrations of plasticizer relative to gelatin and water was determined. See, Id. at p. 63, and FIG. 7. The data was interpolated to estimate the melting-point of plasticized gelatin at its corresponding ERH. The results suggest that as a capsule dries and the ERH of the gelatin decreases, the melting temperature of the gelatin-containing capsule shell increases. The increase in the melting temperature of the capsule shell as the capsule dries allows the drying temperature to be increased during the drying process to drive moisture from the capsule at a faster rate.

Although soft capsules such as the ones discussed above have been successfully used for years as capsules for various materials, such as pharmaceuticals, the use of gelatin in these formulations has several drawbacks, such as incompatibility with certain substances, and a desire to not use gelatin from animal sources. In response to these potential drawbacks, soft capsules have been developed, which are free from gelatin. The soft capsules that do not contain gelatin typically contain carrageenan and/or starch in place of the gelatin. Examples of such soft capsules, and related manufacturing methods can be found in U.S. Pat. Nos. 6,340,473, 6,582,727, and 6,884,060. Numerous other soft capsule formulations that do not contain gelatin are also known in the art and can be dried by the methods and systems of the invention.

The present system and process is applicable to drying both gelatin-containing soft capsules, as well as other types of soft capsules that do not contain gelatin. Similar testing can be used for capsules that do not contain gelatin in order to determine the melting points and corresponding ERH's for a particular capsule formulation to be dried in the drying process described below. "Softgel capsule," and "soft capsule" as used throughout the description refers to both soft capsules that contain gelatin, as well as soft capsules that do not contain gelatin.

Adjustments to the relative humidity of the drying environment can also be used to decrease the drying time. Specifically, the differential between the relative humidity to which the capsules are exposed in the drying system and the equilibrium relative humidity of the capsules (hereinafter "the differential relative humidity or dRH") can be used to drive water from the soft capsule. This dRH can be controlled during the drying process for this purpose. Control of the differential relative humidity can be used to provide a faster drying time compared with conventional drying processes while avoiding the defects normally associated with accelerated drying of soft capsules.

Adjustments to the relative humidity can be used to maintain a higher rate of diffusion of moisture across the soft capsule shell even after a maximum safe drying temperature has been reached. Such a maximum drying temperature may be determined based on factors such as the melting temperature of the particular capsule shell formulation, safety concerns, such as OSHA regulations, and/or other factors.

The Moisture Vapor Transition Rates (MVTRs) of water through a gelatin film at different levels of relative humidity were determined. For this purpose, an MVTR cell was filled with a supersaturated salt solution and surrounded by a gelatin film. The external relative humidity was then reduced stepwise while monitoring the weight loss of the MVTR cell, the salt solution, and the gelatin film as water from the salt solution diffused through the gelatin film. At each external relative humidity, the constant slope of the mass loss was determined. The slope of mass loss at the steady state for each external relative humidity was plotted versus the differential in relative humidity between the internal salt solution and the external relative humidity. The results of this comparison are shown in FIG. 1. The results show that a differential relative humidity of about 25% RH between the relative humidity of the supersaturated salt solution and the external relative humidity provides the fastest rate of water transfer through the gelatin film.

Figure 2:
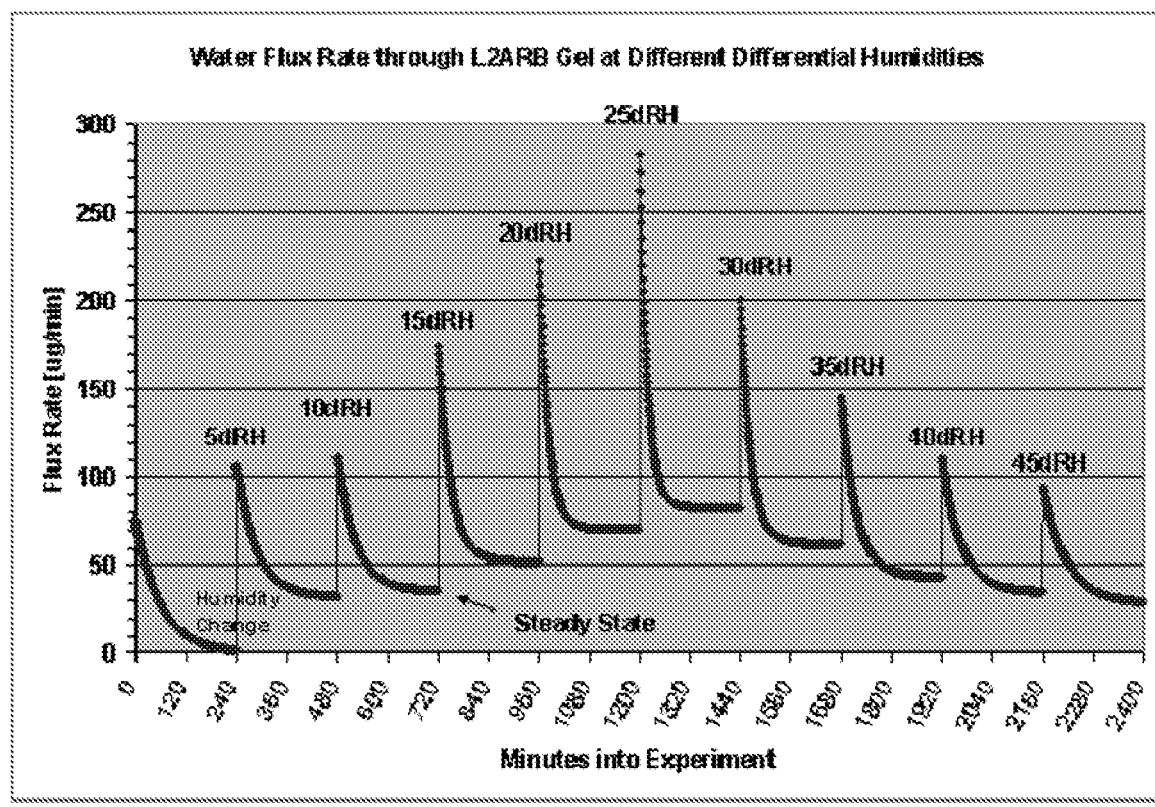
FIG. 2 is a graph showing water flux rate over time at several differentials between the relative humidity in the drying system and the equilibrium relative humidity of a saturated salt solution through a gelatin film.

In the same study it was also observed, that altering the differential relative humidity provided an additional benefit. FIG. 2 shows a plot of the mass loss when the external RH outside of the cell is changed. Upon changing the external RH there is an initial high mass loss that exponentially decreases until the steady state mass loss is reached. The initial mass loss rate is higher than the steady state rate mass loss of the other RH differentials, as seen in FIG. 2. As such, adjusting the external RH can further increase the diffusion rate by providing short periods of high initial diffusion rates that exceed typical steady state diffusion rates prior to the mass loss rate reaching steady state.

Additionally, as noted above airflow velocity also influences the diffusion rate of water across a capsule shell. Air flow can also help maintain a desired temperature in a drying system by removing air from the system that has been cooled by the evaporative cooling that results from evaporation of water from the capsule shell into the air in the drying environment. Evaporative cooling may slow the drying process by reducing the temperature in the drying environment with the use of standard drying equipment, such as drying tunnels.

For example, tunnel dryers typically include high density, large capacity stacks of trays loaded into a tunnel. The tunnel directs air through the trays instead of around the stack, which normally occurs in open air drying or drying rooms. However, much of the airflow in these tunnels still travels around the stacks. Shrouds have been added as a method of redirecting the air back to the stacks, and the use of such shrouds has had positive results. However, with the use of the shrouds, evaporative cooling becomes the limiting factor for soft capsule drying in tunnel dryers. As water evaporates from the capsule, heat is lost through evaporation and this cools the capsules, as well as the surrounding air. The faster the drying, the more pronounced is the effect of evaporative cooling.

Figure 3:
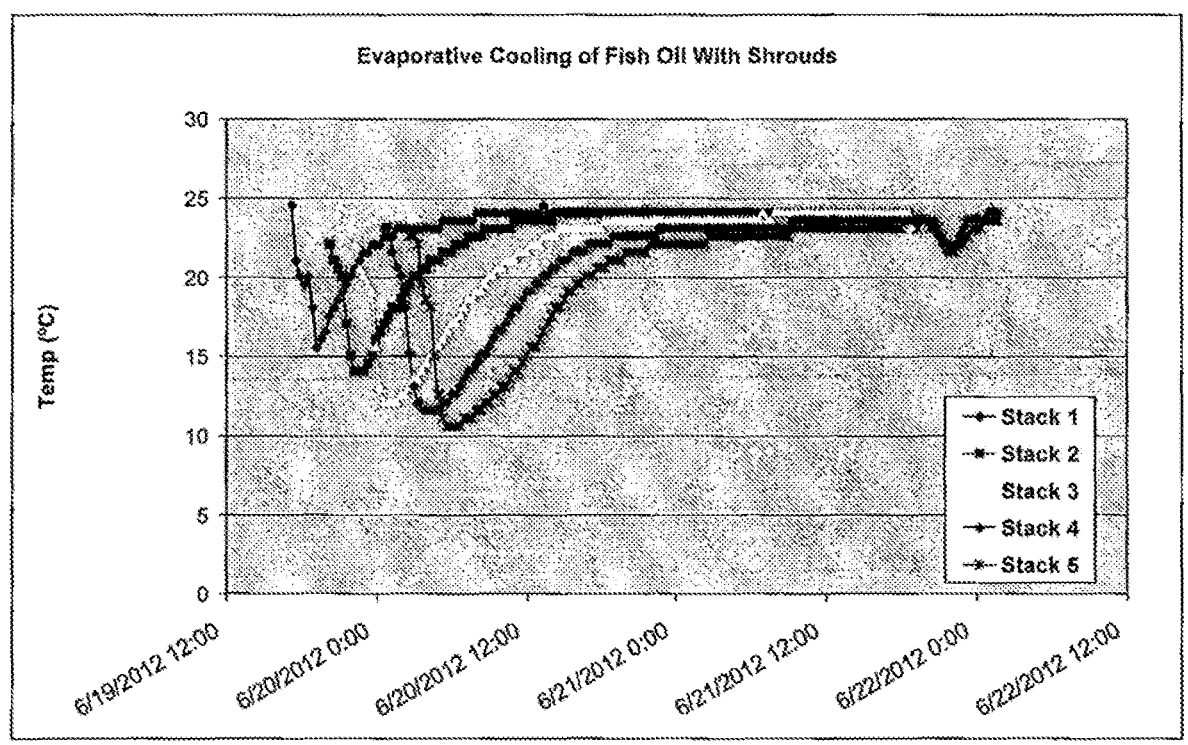
FIG. 3 is a graph showing the temperature effects of evaporative cooling over time of fish oil capsules in a tunnel dryer having shrouds installed.

FIG. 3 shows a graph of the effect of evaporative cooling on the stacks of capsules in a tunnel containing shrouds for redirecting airflow. The cooler air created by evaporation of water from the material in the earlier stacks in the tunnel creates lower temperatures in the later stacks. Depending on the starting temperature and the amount of evaporation in the earlier stacks, the last several stacks in the tunnel can have low air temperatures that are close to, or even reach, the wet bulb temperature of approximately 10° C.

Reducing the humidity of the drying environment has no effect on evaporative cooling. Instead, reducing the humidity reduces the wet bulb temperature and increases utility costs. Data has shown that although evaporation continues at lower temperatures, the evaporation rate is slower. As such, capsules located in the later trays of the drying system will experience slower drying times even if the humidity is reduced due to the reduced temperatures and evaporation rate caused by evaporative cooling.

Further, although increasing the air temperature entering the system can be helpful, evaporative cooling is not thereby reduced or prevented. As such, if the temperature of the air entering the system is maintained at an acceptable temperature for drying the capsules in the initial stacks, the lower temperatures in the later stacks caused by the evaporative cooling still makes it difficult for these later stacks to dry the capsules at the desired rate.

An increased airflow, or recirculation airflow, as in the present invention, can be employed to address the evaporative cooling issue. More specifically, optional adjustments to the airflow can be made during the drying process to compensate for evaporative cooling. Such airflow adjustments can be made in addition to exercising control over the relative humidity and temperature of the drying environment.

In some embodiments, an optional recirculation fan can be included in the drying system. Such a recirculation fan may be positioned and configured to recirculate air from the exhaust back to a supply of air provided to the drying system. The recirculation fan can also be used to control the velocity of the airflow in the drying system. Also, a combination of the recirculation fan and a source of humidity can be used to control the relative humidity in the drying environment.

Providing an airflow through the drying environment can reduce the effects of evaporative cooling by continuously moving cooled air away from the capsules and out the exhaust of the drying system. The removed cooled air can be replaced by warmer incoming air to counter the evaporative cooling effect. The recirculation fan can be used in any type of drying equipment to provide similar benefits.

In some embodiments, a higher velocity airflow is employed during the early stages of drying since the highest rate of evaporative cooling occurs in the early drying stages. As drying progresses, the evaporation rate lessens and hence the rate of evaporative cooling also lessens. As a result, the velocity of the airflow can be reduced during the later stages of drying while still effectively countering the effect of evaporative cooling.

Thus, in some embodiments, controlled variations in the temperature and relative humidity are employed in conjunction with optional changes in airflow velocity in order to ensure faster drying of soft capsules with fewer defects.

Figure 4:
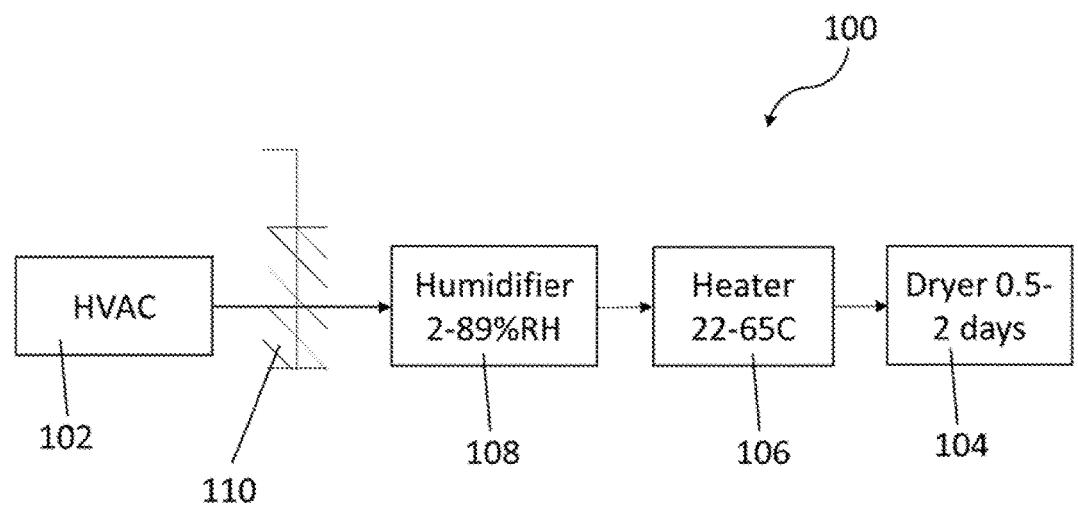
FIG. 4 is a schematic diagram of a drying system according to one embodiment of the disclosure.
Figure 5:
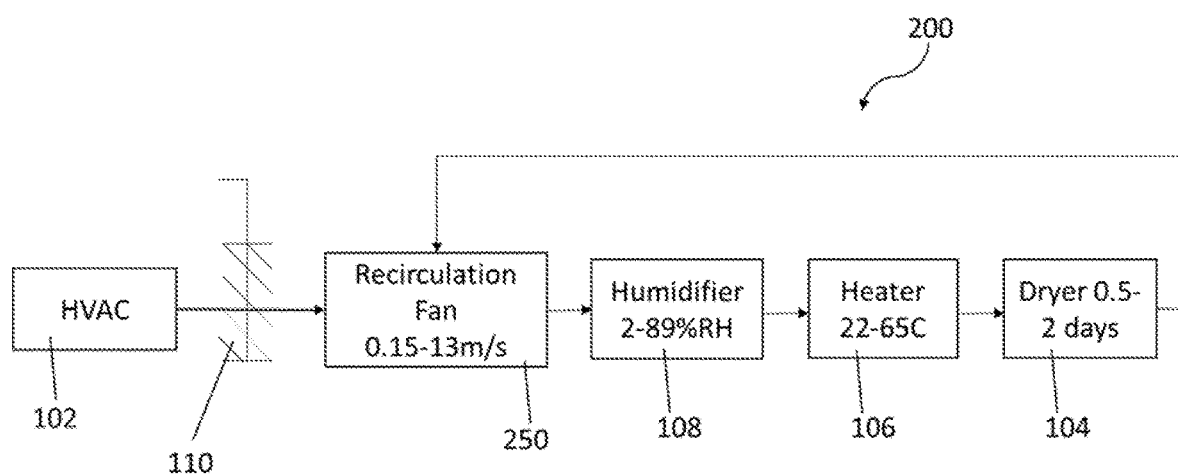
FIG. 5 is a schematic diagram of a second embodiment of a drying system of the disclosure.

FIG. 4 is a schematic diagram of a drying system 100 according to an embodiment of the present invention. In this embodiment, system 100 comprises a HVAC unit 102, standard drying equipment 104, a heater 106, and a humidifier 108. FIG. 5 shows a second embodiment of a drying system 200 of the present invention wherein an optional recirculation fan 250 has been added to the system.

The HVAC unit 102 may optionally comprise a dehumidifier, and is used to supply cool dry air through the drying system. The HVAC unit 102 may be directly connected to a damper to supply only fresh air to the drying system, or air can be pulled-in from and released back into the room comprising the drying equipment. As shown in FIG. 5, a recirculation fan may also be used to recirculate air leaving the drying equipment to mix with air entering the drying equipment. Recirculated air only, fresh air, air from the drying room provided by the HVAC unit, or any combination of the foregoing air sources may be used in the drying equipment. The humidity of the air supplied from the HVAC unit can range from about 5% RH to about 30% RH. The RH of the air provided by the HVAC unit is preferably lower than the desired RH of the air within the drying equipment. As such the air provided by the HVAC unit is considered "dry air."

The temperature of the air entering the system from the HVAC unit can range from about 20° C. to about 29° C., and the desired temperature can generally be chosen based on a comfort level of the room where the drying equipment is located. Preferably, the temperature of the air from the HVAC unit is between about 22° C. and about 26° C., and most preferably the temperature is about 23° C. to about 25° C.

Between the HVAC system and the drying equipment is an optional flow control valve 110. Flow control valve 110, if used, can be set, manually adjusted, or controlled through the use of sensors to close or reduce the size of an inlet orifice when restriction of the dry air flowing into the system is desired.

The drying equipment may be any standard drying equipment known in the art, including, but not limited to any form(s) of, drying conveyors, tumble dryers, fluid bed dryers, drying tunnels, or drying rooms. The system or method disclosed herein is independent of the type of drying equipment used.

The humidifier supplies humidity to the system. The humidifier may include, steam generation, ultrasonic mists, wicks, or packing. As noted above, the wet capsules themselves provide some humidification in the drying environment by evaporation of water from the capsules. The optional use of recirculation airflow can capture humidity exiting the drying environment and return it to the system. The initial relative humidity of the system is high as the wet capsules are introduced to the system and the relative humidity of the system decreases over time as the capsules dry. Relative humidity ranges useful for accelerated drying can range from 2-89% RH depending on the type of capsules being dried. For example, capsules with lipophilic fills, also referred to as lipophilic capsules, are preferably dried using a lower % RH than capsules with hydrophilic fills, also referred to as hydrophilic capsules.

For lipophilic capsules the initial relative humidity range is preferably from 49% RH to 79% RH and the end point relative humidity range is preferably from about 2% RH to about 36% RH. More preferably, the initial relative humidity range for lipophilic capsules is from about 59% RH to about 69% RH and the end point relative humidity range for lipophilic capsules is from about 10% RH to about 24% RH.

For capsules with hydrophilic fills the initial relative humidity range is preferably from about 49% RH to about 79% RH and the end point relative humidity range is preferably from about 15% RH to about 58% RH. More preferably, the initial relative humidity range for hydrophilic capsules is from about 59% RH to about 69% RH and the end point relative humidity range for hydrophilic capsules is from about 23% RH to about 57% RH.

The temperature of the drying environment may be maintained by use of a heater. Heat may be provided, for example, by one or more of the following methods, heating though heating elements, dissipative heat from motors, lights, or by friction forces generated by the process itself. The drying temperature must be maintained below the melting temperature of the specific soft capsule formulation being dried. As mentioned above, the melting temperature of the capsule shell increases as the capsules dry, and thus the drying temperature can be increased over time as this melting temperature increases. The overall temperature range useful for the accelerated drying system can range from about 22° C. to about 68° C. Preferably, the temperature range is from about 32° C., which is the melt temperature of most wet gelatin shells to about 48° C., which is a typical maximum temperature that can be used in compliance with Occupational Health and Safety Administration standards. However with proper insulation and capsule shells with sufficiently high melting points, it is possible in some circumstances to be able to use even higher temperatures to drive faster drying. Further, in some special cases, lower temperatures can be used depending primarily upon the specific formulation of the soft capsule.

If an optional recirculation fan is used, the fan may be a part of the HVAC unit, or the fan may be a separate part of the drying system. Recirculation is optional, but it may be used to help maintain the desired temperature and relative humidity in the drying system, and can also be used to reduce energy costs. The fan speed of the recirculation fan may be adjusted to match the system being used, and the fan may be operated in a manner whereby the velocity of air across the soft capsule is from about 0.15 m/s to about 13 m/s, preferably, from about 0.15 m/s to about 8.3 m/s, and most preferably, from about 0.35 m/s to about 2.5 m/s. Depending on the type of drying equipment being used, fan speed can be adjusted. For example, for fluid bed drying, greater fan speeds may be required to provide a beneficial effect, but in these types of dryers increasing airflow has limited effects on drying, while increasing electrical costs. As such, the benefits of increased airflow must be weighed against the cost of operating the fan.

A reduction in the velocity of airflow over the capsules resulting from reduced fan speed will cause an increase the relative humidity surrounding the capsules as moisture from the capsules continues to evaporate. As a result, manipulation of the fan speed may also be used for control of the relative humidity in the drying environment as the drying process progresses, as well as to reduce the effect of evaporative cooling. Thus, in some embodiments, the fan speed will be decreased over time, either constantly or intermittently in order to maintain a fan speed that ensures a consistent, desired relative humidity level in the drying system.

To use the drying system as disclosed herein, and shown in FIGS. 4 and 5, soft capsules that require such drying are first produced according to standard procedures. The wet capsules are then located in the drying equipment, and the drying system is operated. The temperature, relative humidity and optional airflow is adjustable by hand, by a preprogrammed system, or can be adjusted based on data obtained in real-time from the system, or by a pre-programmed controller to provide a ramp of temperature, relative humidity, and optionally, airflow velocity based on the specific soft capsule formulation being dried, local environmental conditions and the desired drying time.

The initial temperature within the drying equipment is selected based on the specific soft capsule formulation used in the capsule shell. The temperature should be selected to be close to, but at least 2-3° C. below the melting point of the specific soft capsule formulation. For example, the temperature can be maintained from 2-10° C., or 2-7° C. or 2-5° C., or 3-8° C. or 3-6° C., or most preferably, 2-3° C. below the melting point of the soft capsule shell during the drying process. To maintain this temperature differential, the temperature in the drying system will have to be increased as the melting point of the capsule shell increases due to drying. The melting point of the soft capsule formulations is determined in the laboratory at varying water concentrations. Sorption curves can be developed to correlate the water concentration and equilibrium relative humidity. Therefore, using such sorption curves, the melting point of the capsule can be determined in real-time during the drying process by monitoring the equilibrium relative humidity.

Over time, as the capsules dry, the equilibrium relative humidity of the capsule decreases and the melting point of the soft capsule formulation increases. As the melting point increases, the temperature within the drying equipment is increased to maximize moisture removal from the capsules per unit time. The temperature is preferably controlled through the use of a heater and an optional chiller.

Since the temperature of the air provided to the system the HVAC unit is likely lower than the desired drying temperature, the heater within the system is used to increase the air temperature inside the drying equipment to the desired set point. Additionally, if an optional recirculation fan is used, recirculation of air leaving the heating equipment to the air entering the heating equipment can be used to conserve heat and help to maintain the desired set point temperature. After some time, the temperature in the system may plateau due to safety concerns, or other factors.

The capsules are cooled down to room or ambient temperature once the drying process is complete, or nearly finished. For this purpose, an optional chiller may be included, or an additional amount of the cooler air from the HVAC system can be allowed to enter the drying equipment.

While the temperature is being adjusted, the relative humidity within the drying equipment is also being controlled. Humidity control is used to preserve the quality of the heated capsules. The relative humidity starts at a high value and is decreased over time as the capsules dry.

Preferably, the relative humidity is controlled by a humidifier and/or a recirculation fan. Humidity is provided to the system by a humidifier, or by the moisture evaporating from the capsules or by recirculated air. A flow control valve 110 can also be employed on the air inlet from the HVAC equipment to reduce, or prevent the flow of air having a lower relative humidity from entering the drying equipment in order to further control the relative humidity.

The relative humidity is adjusted to maintain a differential relative humidity across the shell of the capsule of about 15% dRH to about 35% dRH, more preferably from approximately 20% dRH to about 30% dRH, and most preferably, the differential relative humidity is approximately 25% dRH. The relative humidity in the drying system is lowered as the capsules dry to maintain this differential relative humidity. However, if the temperature is no longer increasing, due to safety or other reasons, the relative humidity can be varied to change the differential relative humidity in order to alter (e.g. increase) the rate of evaporation from the capsules.

Figure 6:
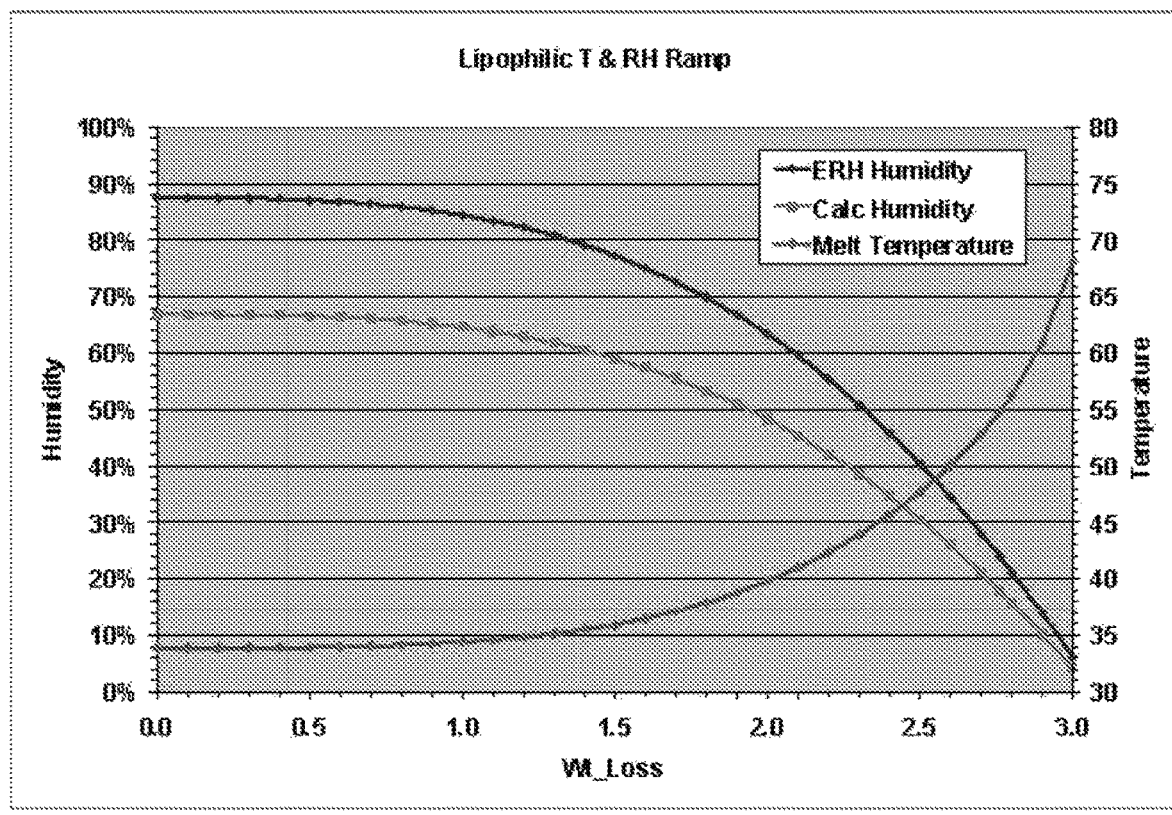
FIG. 6 is a graph showing an example of a temperature and relative humidity ramp according to an embodiment of the disclosure.

An example humidity and temperature ramp for a lipophilic capsule is shown in FIG. 6. A similar curve can be produced for a hydrophilic capsule. The curve for the hydrophilic capsule will typically have a less steep slope than the curve for the lipophilic capsule. The final humidity of hydrophilic capsules is typically between 53% and 57% due to internal differences in fill formulation. The temperature remains below the melting temperature of the soft capsule formulation, which increases as the capsule dries. The increase in temperature over time helps to evaporate moisture from the capsules.

Each adjustment in temperature and/or humidity can be made through a program based on the material properties of the specific soft capsule formulation, or can be based on data received from one or more sensors located within the system. A preferred method of selecting the temperature and/or relative humidity over time is based on the equilibrium relative humidity of the capsules, but other methods can also be used, such as measuring the weight loss of the capsules.

The ERH of the capsule can be measured in real time. Based on the correlation between the ERH and melt temperature of the soft capsule, the ERH is then plotted on a graph showing the relative humidity and temperature ramp, or entered into an equation based on a calibration graph. The corresponding values can be used to determine the temperature and relative humidity set points for the system over time.

The initial relative humidity is high based on the high ERH for the manufactured capsules and is typically from about 45% RH and 90% RH. Further, the endpoint relative humidity for each soft capsule is controlled and may be customized for each formulation. For example, for fish oil capsules an endpoint relative humidity of 10% RH-24% RH is desirable. For ibuprofen capsules an end point humidity of 23% RH-57% RH is desirable.

Using the present system, a typical fish oil capsule can be dried to a hardness of >8N in nine hours, and a typical ibuprofen capsule can be dried to a fill moisture of <7.5% in forty-eight hours. These values represent a 60-80% drying time reduction over a typical softgel drying process, which usually takes from 2-10 days depending on the specific formulation.

Once the capsules are dried to the desired moisture content, they are removed from the drying equipment. The end point of the drying process can be determined by capsule hardness, weight loss, fill moisture determined by Karl Fischer method, capsule moisture determined by Loss on Drying (L.O.D.), or other methods known in the art.

Figure 7:
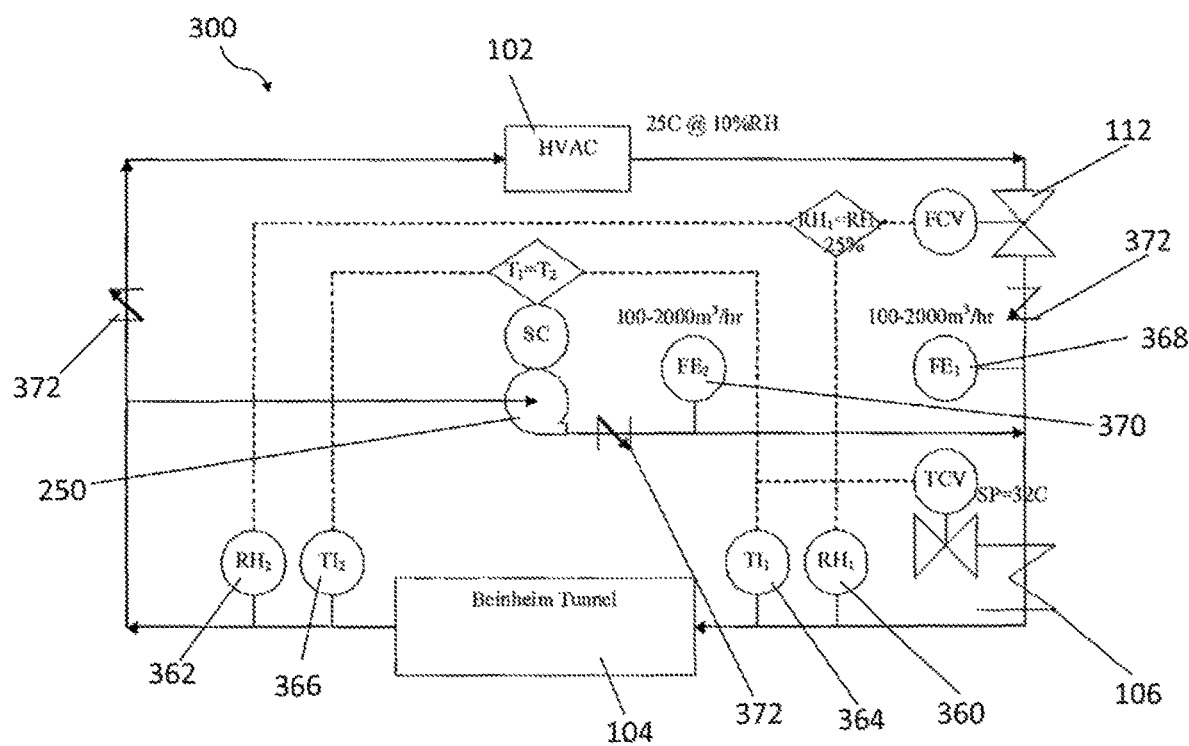
FIG. 7 is a modular control system for controlling the drying system of FIG. 5.

FIG. 7 shows a schematic of a preferred control system 300 for a drying system as shown in FIG. 5 using a tunnel dryer as the drying equipment. The HVAC system preferably provides air at 25° C. and 10% RH. However, the parameters of air temperature and relative humidity can be varied depending on room comfort levels, and desired relative humidity levels for drying the specific product.

Three different pairs of sensors can be used in this preferred system. The first pair of sensors measures the relative humidity of the supply air 360 and the return air 362. Preferably, a differential relative humidity within the drying equipment is maintained at approximately 25% dRH. If desired, the relative humidity of the supply air can be controlled and maintained at slightly higher levels to minimize product defects when higher temperatures are used to increase the rate of drying. The differential relative humidity can be set at a single value, or can be altered throughout the process to influence the drying time.

To control the relative humidity, a flow control valve 112 can be used on the duct from the HVAC unit 102. The relative humidity of the air entering the system from the HVAC unit 102 is low, and for this embodiment is about 10% relative humidity. Therefore, by reducing the amount of flow from the HVAC, the relative humidity of the supply air will be increased. The supply air relative humidity sensor 360 may be used to obtain measurements that provide information for controlling the flow control valve 112 based on a single loop controller to maintain the desired differential relative humidity within the drying equipment.

To maintain a differential humidity of 25% dRH and maintain a minimum humidity of 15% RH, which is the minimum where the HVAC valve begins to close, the following algorithm may be used:

=IF(RH1>MIN,(IF(RH2<(DIFF+DIFF),(RH2−MIN), DIFF),(RH2−MIN))

RH1: Relative humidity from the supply sensor
RH2: Relative humidity from the return sensor
DIFF: Desired differential relative humidity
MIN: Minimum humidity set point At this point the differential relative humidity would be recalculated to ensure that RH1 does not drop below the minimum set point.

The second pair of sensors includes temperature control sensors 364 and 366. A heat exchanger or other heating element 106 is installed into the supply duct of the drying equipment 104. The air supply temperature sensor 364 controls the heat transfer based on a single loop controller to maintain and control the supply side temperature. As discussed above, the temperature values can be set to ramp up to increase diffusion of water from the gel, while remaining below the melting temperature for the specific soft capsule formulation.

The third set of sensors 368, 370 used in this embodiment of a control system 300 is a set of air flow control sensors. Increasing air flow has been shown to minimize the effects of evaporative cooling, and decrease drying times as described above. The air flow sensors can be used to obtain information to be used for controlling the flow coming from the HVAC system alone, or preferably a recirculation fan is also used in the system. The addition of a recirculation fan increases the velocity of the air across the capsules. Operation of the recirculation fan is based on an algorithm that minimizes the difference between the supply and return temperatures monitored by the temperature sensors by controlling the fan speed.

| Differential Temperature [C.] | Fan Control [%] |
|---|---|
| <1 C. | 0 |
| >1 C. | 100 |

Where, if the temperature at the exhaust temperature sensor 366 is less than the temperature at the inlet temperature sensor 364 by 1° C. the fan fan is started or the fan speed is increased. The recirculating fan and the HVAC system preferably each provide air flow between about 100 m$^3$/hour and about 2000 m$^3$/hour. Several check valves 372 are also located throughout the system to prevent backflow into the HVAC unit, the drying equipment, and/or the recirculation duct. The recirculation fan also provides air having a higher humidity and temperature to the supply air as compared to the air provided by the HVAC unit.

Although the above control system has been described in terms of varying the temperature, relative humidity and air flow, it is understood that a reduction in drying time can be achievable through the use of any one or more of these elements. Further, any combination of two of the above elements can also provide a reduction in drying time. Preferably, the system uses a combination of temperature control and humidity control to reduce the drying time of soft capsules and produce capsules with acceptable physical properties.

The following examples are illustrative, but not limiting, of the present disclosure. Other suitable modifications and adaptations of the variety of conditions and parameters normally encountered in the field, and which are obvious to those skilled in the art, are within the scope of the disclosure. The following examples illustrate the practice of the present invention in some of the preferred embodiments.

EXAMPLES

Example 1

Lipophilic Capsule Drying Time

The effect of changing the relative humidity and temperature on the rate of capsule drying of lipophilic capsules was measured. A control was run using a standard drying tunnel. The temperature of the standard drying tunnel was 22° C. and the relative humidity of the standard drying tunnel was 12% RH at the start of the process. Samples were placed on a tray with tray paper, built into a partial stack, and placed into tunnels. Samples of capsules were taken every 6 hours to test hardness.

Two comparison experiments were conducted using a tumble dryer. A baseline for the tumble dryer was obtained by use of a CS-TJS-1 large basket continuous tumble dryer. The basket loads were limited to 60 kg and 100 kg with a midpoint of 80 kg, and rotation speeds of 3 rpm and 6 rpm were employed, with a midpoint of 4.5 rpm. The relative humidity was kept at 12% RH for the baseline experiment and the temperature was maintained at 24° C. A second comparison study was conducted with the same equipment and same parameters, but with the temperature maintained at 35° C.

Data loggers were used to capture the temperature and relative humidity inside the tumble dryer baskets as well as on the intake filter and exhaust of the tumble dryer. Sample capsules were taken to measure the capsule weight and equilibrium relative humidity (ERH) before each run, and hardness, weight loss, and ERH were also measured every 1-2 hours for the first 6 hours and every 6-12 hours after that for the two comparison experiments.

Figure 13:
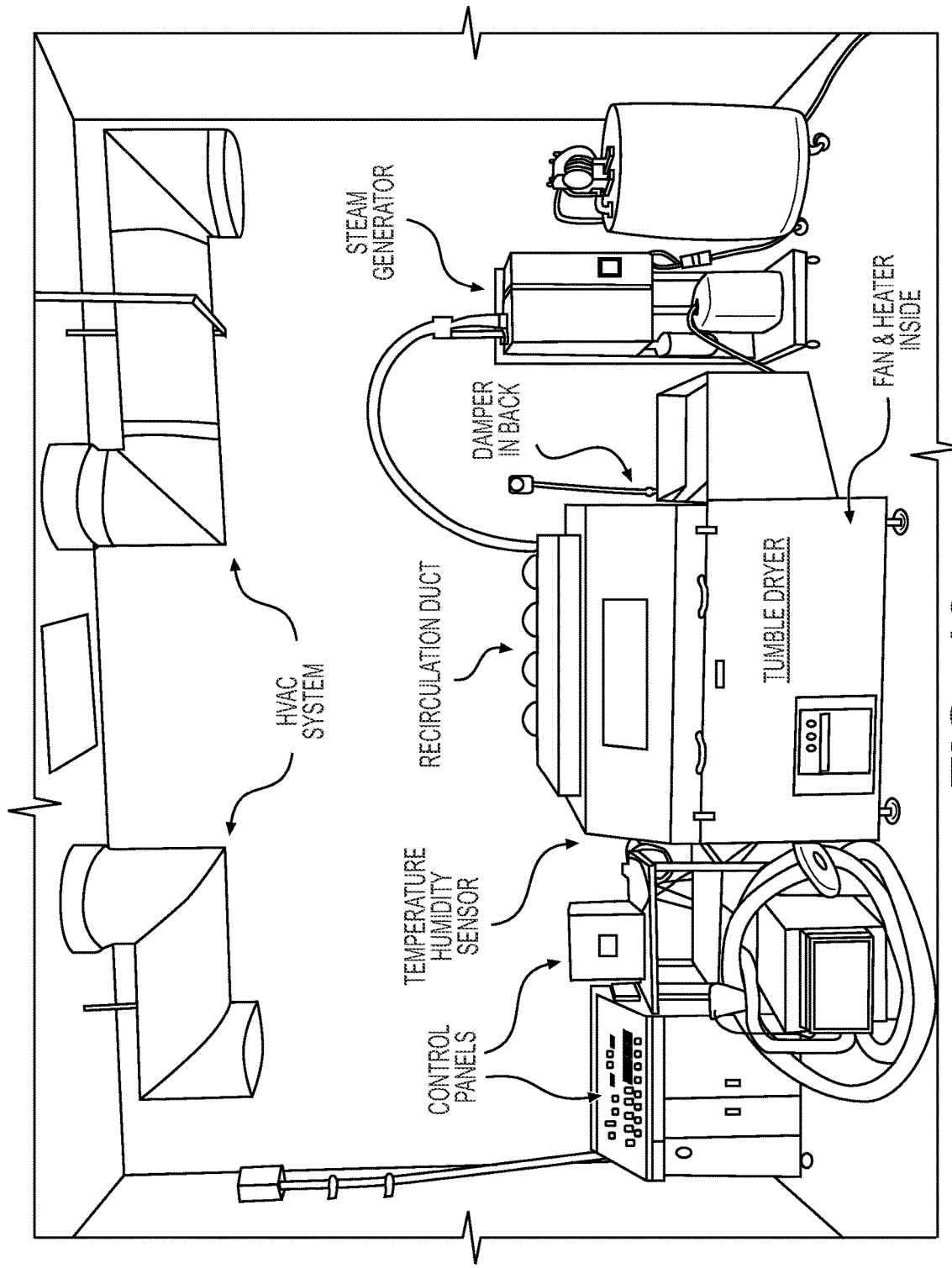
FIG. 13 is a photograph of a tumble dryer modified according to an embodiment of the disclosure.

For the experimental studies, the CS-TJS-1 large basket continuous tumble dryer was modified to include a temperature and relative humidity control system. A modified tumble dryer is shown in FIG. 13. The other parameters were all kept the same as for the comparison experiments. The temperature and relative humidity control system included a recirculation duct, a damper, and a steam generator to conserve heat energy and add humidity to the system. The temperature and relative humidity in the tumble dryer housing were measured using a calibrated Vaisala transmitter. Airflow was heated using heating elements located inside the tumble dryer. Humidity was added using a Nortec steam generator. The ERH of the capsules was measured using Aqualabs water activity meter where four capsules are placed in a closed container and relative humidity measured until a minimal rate of change in humidity is detected. The temperature and humidity in the interstitial sites between the capsules was monitored using the iButton data logger in a nylon bag.

Samples were taken every hour and the weight of 10 capsules was measured and averaged. The weight loss was calculated from the initial weight. The weight loss was plotted on the graph shown in FIG. 8 from which new temperature and relative humidity set-points were determined and entered. For this experiment, estimates for ERH and temperature were made from data previously obtained for the specific soft capsule formulation as shown in the graph of FIG. 6, and melt temperature was calculated directly from the ERH of the capsule regardless of the weight loss. Four different temperature/humidity ramps were conducted, all using variations of the graph as shown in FIG. 6.

An additional control studies were conducted using the CS-TJS-1 large basket continuous tumble dryer. The control study followed the same protocol as the experimental procedure, but only included a temperature ramp, without relative humidity control. By using temperature alone, the capsules dented upon cool down. Capsules with both temperature and humidity control did not affect the quality of the capsule. Therefore it can be concluded that both temperature and humidity control are needed to accelerate drying.

Figure 8:
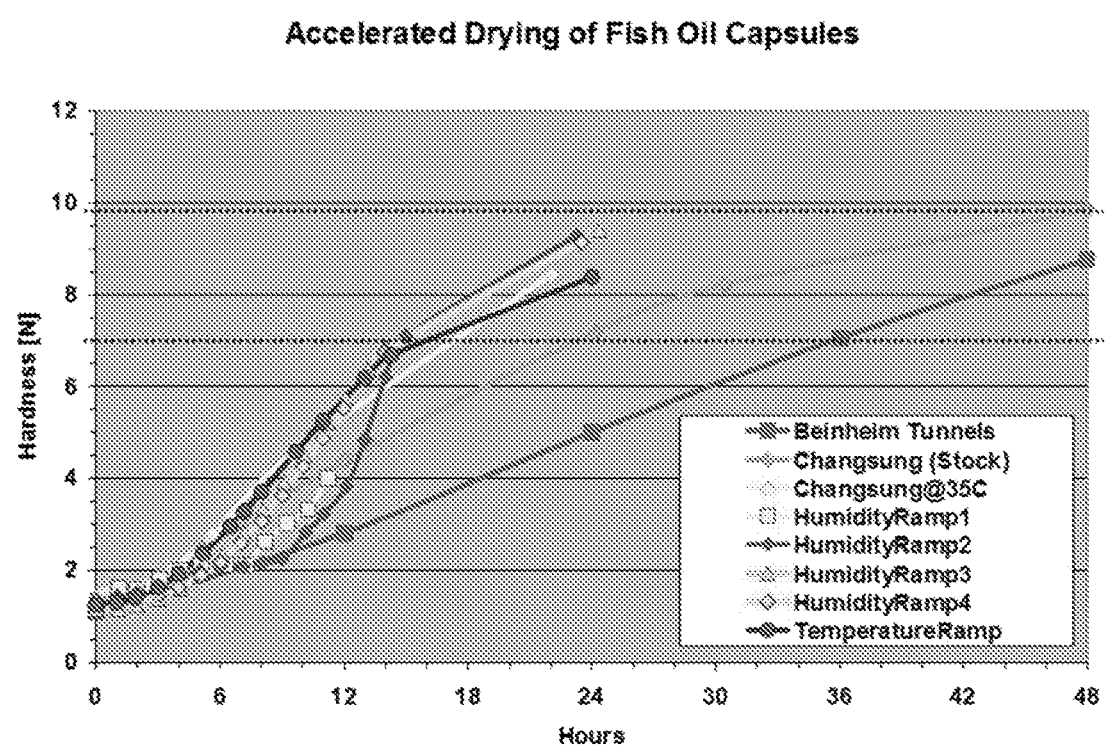
FIG. 8 is a graph showing the hardness's of lipophilic capsules over time during various drying processes.

The results of this Example are shown in FIG. 8. The hardness of the samples was measured using a Bareiss Digitest Gelomat. The hardness specification of this particular product was between 7-10 N. The results showed that the use of temperature and relative humidity control reduced the drying time from approximately 36 hours for the drying tunnels, to approximately 12 hours. It also cut the drying time for the standard tumble dryers by more than 50%. Using more precise control of relative humidity and temperature should allow a further reduction in the drying time.

Example 2

Hydrophilic Drying Time

Figure 9:
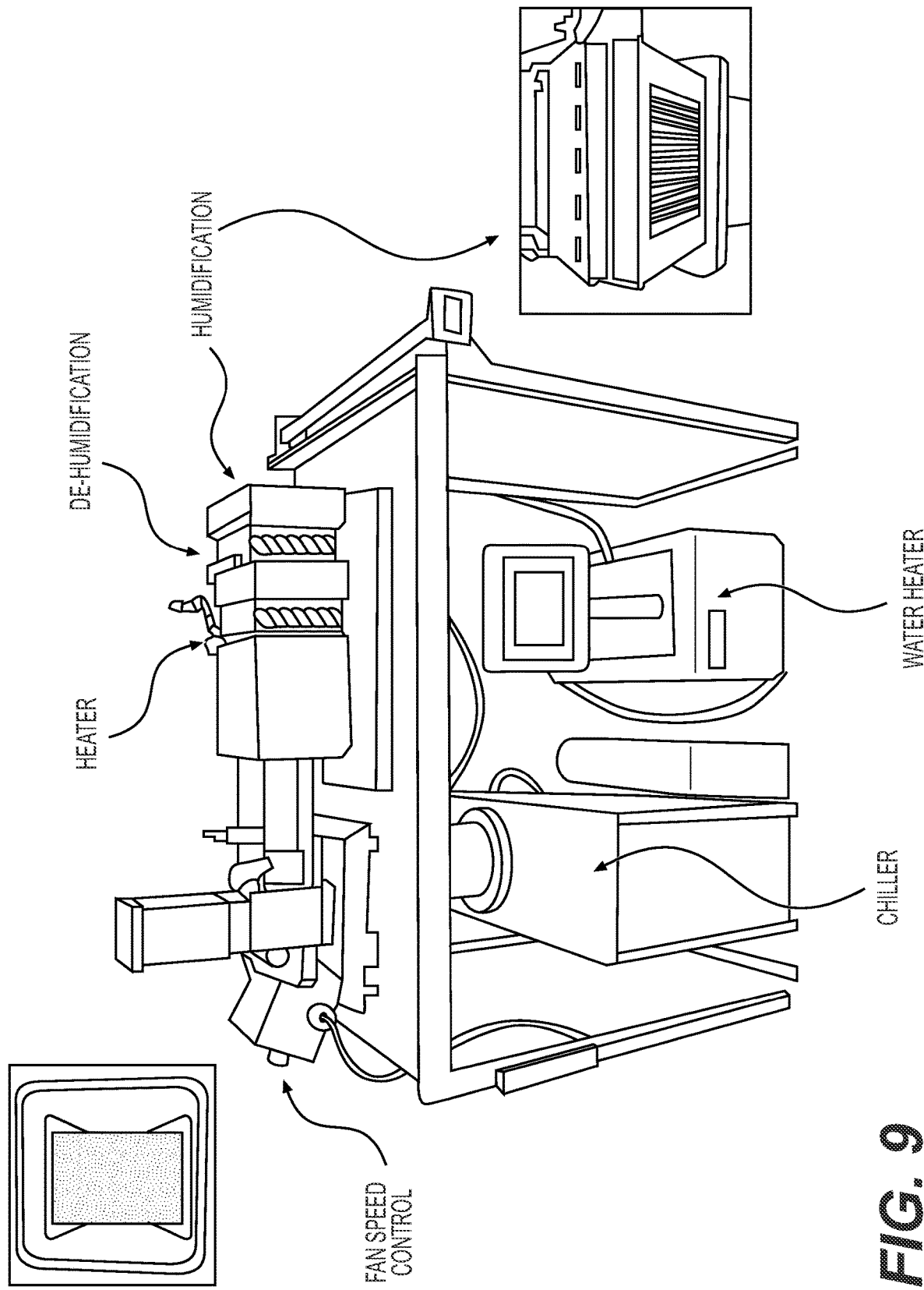
FIG. 9 is a photograph of a fluid bed dryer modified according to an embodiment of the disclosure.
Figure 10:
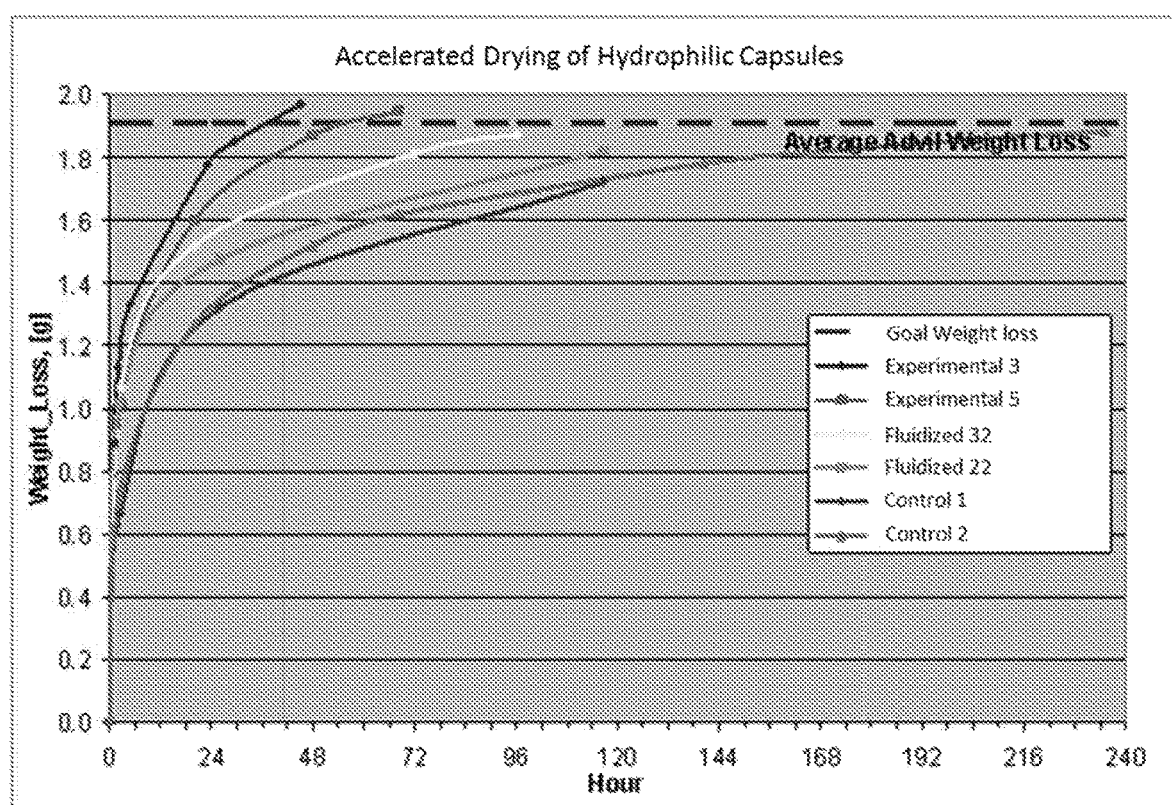
FIG. 10 is a graph showing weight losses of hydrophilic capsules over time during various drying processes.

The effect of changing humidity and temperature on the rate of capsule drying for hydrophilic capsules was tested using a lab scale fluid bed dryer as shown in FIG. 9. This study was also used to observe the quality of the final hydrophilic product. The temperature and relative humidity control for this experiment was exercised manually and, as such, was not precise, but the results still showed an 80% drying improvement over the control drying run was achieved by decreasing the drying time from 10 days to 2 days. The results for the drying time for the control and comparison samples versus two experimental samples are shown in FIG. 10. Table 1 below shows the parameters for temperature, relative humidity and air flow that were used for each of the tests.

For the control experiment, hydrophilic capsules were placed in a weigh boat with a napkin on top at ambient conditions. The weight of 10 capsules was measured and the time of each measurement was recorded.

Comparison experiments were conducted to compare the results using the temperature and relative humidity control of the present invention to the use of a fluidized bed dryer at two different temperatures (fluidized 22 and fluidized 32). For the comparison fluidized bed dryer experiments, the air flow was maintained at approximately 12 m/s throughout the experiment. For fluidized 22, the temperature was maintained at approximately 22° C. The humidity was not adjusted and varied between 10.9% RH and 14.8% RH. These temperature and humidity conditions were the same as the "ambient conditions" used for the control.

For the fluidized 32, the humidity was not controlled and was measured at between 5.2% RH and 8.0% RH during the experiment. The temperature was maintained at approximately 32° C. through the use of a heater. The lower relative humidity can be explained by the higher temperature used in this comparison experiment.

Two different experimental batches were compared with the two control samples and two comparison examples for rate of drying. The two Experimental tests are labeled Humidity 2 and Humidity 5 in Table 1. The air flow was not fluidized and was maintained below 1 m/s for these experiments so that the temperature and humidity control could be evaluated. The temperature and relative humidity were adjusted throughout the experiments. Each experimental run utilized a different equation based on melting point and ERH for the specific softgel formulation to correlate the weight loss to the next humidity set point. For the first experimental batch the temperature was ramped up from approximately 30° C. to approximately 45° C., after which the temperature was brought back down to 25° C. The relative humidity was maintained at a high level throughout the experiment and ranged from 75% RH to 30% RH and generally decreased as the temperature increased.

For the second experimental batch the temperature was ramped up from approximately 30° C. to approximately 42° C., after which the temperature was brought back down to 25° C. The relative humidity was also maintained at a high level throughout the experiment and ranged from 70% RH to 40% RH as the temperature increased. The difference between the first experimental test and the second experimental test was the specific set points that were used after each measurement.

Weight loss was measured over time. The hydrophilic capsules were considered dry when there was 1.9 g of weight loss/10 capsules.

Several additional batches were also tested with varying temperatures, fluidization air flow and humidity. The parameters used for each of these experiments are shown in Table 1. Each of the capsules was visually inspected upon completion of the process. The results of these visual observations are also included in Table 1.

TABLE 1

|  | Date | Time | Weight (g) | Air Flow (m/s) | Temp (° C.) | Humidity (%) | Observations |
|---|---|---|---|---|---|---|---|
| Control 1 | 5/22 | 13:40 | 10.189 | Room Conditions | | | Not too Dry only 5 days some shape defects |
|  | 5/22 | 16:11 | 9.525 | | | | |
|  | 5/23 | 15:45 | 8.866 | | | | |
|  | 5/28 | 10:30 | 8.466 | | | | |
|  | Weight Loss = | | 1.723 | | | | |
| Control 2 | 5/27 | 14:23 | 10.148 | Room Conditions | | | dry/clear/blue-green/shiny 10-days |
|  | 5/27 | 17:15 | 9.403 | | | | |
|  | 5/28 | 10:45 | 8.875 | | | | |
|  | 5/29 | 14:31 | 8.628 | | | | |
|  | 5/30 | 10:44 | 8.529 | | | | |
|  | 6/2 | 10:55 | 8.367 | | | | |
|  | 6/3 | 10:59 | 8.333 | | | | |
|  | 6/4 | 10:26 | 8.306 | | | | |
|  | 6/5 | 11:10 | 8.283 | | | | |
|  | 6/6 | 9:32 | 8.265 | | | | |
|  | Weight Loss = | | 1.883 | | | | |
| Fluidized 22 | 5/22 | 13:40 | 10.212 | 12.59 | 22.4 | 10.9 | case hardened/leather/shape defects |
|  | 5/22 | 16:11 | 9.196 | 13.1 | 22.9 | 14.8 | |
|  | 5/23 | 15:45 | 8.736 | 12.51 | 23 | 12.2 | |
|  | 5/27 | 10:30 | 8.389 | 13.31 | 22.2 | 13.1 | |
|  | Weight Loss = | | 1.82 | | | | |
| Fluidized 32 | 5/30 | 10:56 | 10.142 | 11.56 | 30.3 | 7.5 | too dry? Less case hardening/skinny |
|  | 5/30 | 13:40 | 9.077 | 12.16 | 30.7 | 8 | |
|  | 6/2 | 10:49 | 8.329 | 12.34 | 31 | 7.1 | |
|  | 6/3 | 10:59 | 8.268 | 12.54 | 31 | 5.2 | |
|  | Weight Loss = | | 1.874 | | | | |
| Fluidized w/MTB Ramp | 5/27 | 14:37 | 10.071 | 12.69 | 30.8 | 7.6 | rough dimpled 41° C. |
|  | 5/27 | 17:15 | 9.058 | 11.91 | 31.3 | 8 | |
|  | 5/28 | 10:45 | 8.473 | 11.69 | 36 | 6 | |
|  | 5/29 | 14:31 | 8.204 | 11.34 | 40.1 | 2.4 | |
|  | 5/30 | 10:44 | 8.126 | 11.67 | 40.5 | 2.6 | |
|  | Weight Loss = | | 1.998 | | | | |
| Fluidized w/Fast Ramp | 6/3 | 11:12 | 10.247 | 12.45 | 31.8 | 4.8 | rough dimpled 49° C. too high |
|  | 6/3 | 12:08 | 9.356 | 12.56 | 31.7 | 4.2 | |
|  | 6/3 | 13:22 | 9.118 | 11.32 | 38.1 | 2 | |
|  | 6/3 | 16:10 | 8.911 | 11.24 | 39 | 1.6 | |
|  | 6/4 | 10:21 | 8.469 | 11.61 | 40 | 1.5 | |
|  | 6/4 | 16:39 | 8.376 | 10.63 | 43.6 | 3.1 | |
|  | 6/5 | 8:52 | 8.276 | 11.41 | 44.2 | 1 | |
|  | 6/5 | 11:04 | 8.26 | 10.89 | 48.2 | 1.2 | |
|  | Weight Loss = | | 1.987 | | | | |
| Tunnel 32 | 6/5 | 13:47 | 10.512 | 0.45 | 31 | 6.7 | |
|  | 6/5 | 15:10 | 9.48 | 0.35 | 30.8 | 13.5 | |
|  | 6/5 | 16:56 | 9.289 | 0.36 | 32 | 7.1 | |
|  | 6/6 | 9:30 | 8.845 | 0.39 | 32.4 | 6.3 | |
|  | 6/9 | 10:10 | 8.476 | 0.37 | 32.3 | 7.5 | |
|  | Weight Loss = | | 2.036 | | | | |
| Experimental 1 | 6/9 | 11:13 | 10.323 | <1 | 30.8 | 58.9 | somewhat clear some/shape defects/pits (melt) |
|  | 6/9 | 13:10 | 9.253 | | 32.2 | 60.4 | |
|  | 6/9 | 14:58 | 9.082 | | 33.6 | 40.4 | |
|  | 6/9 | 16:25 | 8.962 | | 35.6 | 39 | |
|  | 6/10 | 8:56 | 8.628 | | 35.7 | 29.4 | |
|  | 6/10 | 11:06 | 8.597 | | 38.2 | 35.3 | |
|  | 6/10 | 14:25 | 8.555 | | 38.2 | 33.8 | |
|  | 6/10 | 17:23 | 8.823 | | 39.7 | 29.5 | |
|  | 6/11 | 9:00 | 8.4 | | 39.2 | 6.8 | |
|  | 6/11 | 10:48 | 8.393 | | 41.8 | 35.4 | |
|  | Weight Loss = | | 1.93 | | | | |
| Experimental 2 | 6/11 | 14:47 | 10.161 | <1 | 31.2 | 55 | somewhat clear some/shape defects/pits (melt) |
|  | 6/11 | 15:41 | 9.302 | | 32.3 | 51 | |
|  | 6/11 | 16:53 | 9.062 | | 36.9 | 46 | |
|  | 6/12 | 8:59 | 8.53 | | 31.6 | 41.9 | |
|  | 6/12 | 11:43 | 8.489 | | 40.5 | 42.2 | |
|  | 6/12 | 15:59 | 8.435 | | 40.8 | 43.8 | |
|  | 6/13 | 8:45 | 8.177 | | 42.9 | 1 | |
|  | Weight Loss = | | 1.88 | | | | |
| Experimental 3 | 6/16 | 11:23 | 10.324 | <1 | 30.3 | 54.8 | Green but dull too hot |
|  | 6/16 | 12:41 | 9.39 | | 31.6 | 55.1 | |
|  | 6/16 | 14:42 | 9.171 | | 33.2 | 49.5 | |
|  | 6/16 | 16:59 | 9.048 | | 35 | 45 | |
|  | 6/17 | 8:49 | 8.653 | | 40.3 | 34.4 | |
|  | 6/17 | 16:34 | 8.555 | | 41.7 | 30.2 | |
|  | 6/18 | 9:16 | 8.417 | | 44.1 | 37 | |
|  | 6/18 | 13:18 | 8.4 | | 38.8 | 38.8 | |
|  | 6/18 | 14:34 | 8.396 | | 30.8 | 23.7 | |
|  | 6/18 | 17:04 | 8.392 | | 28.8 | 27.6 | |
|  | Weight Loss = | | 1.93 | | | | |

TABLE 1-continued

|  | Date | Time | Weight (g) | Air Flow (m/s) | Temp (° C.) | Humidity (%) | Observations |
|---|---|---|---|---|---|---|---|
| Experimental 4 | 6/19 | 10:20 | 10.18 | <1 | 29.4 | 76.1 | Green but dull too hot |
|  | 6/19 | 11:30 | 9.385 |  | 32.7 | 65 |  |
|  | 6/19 | 13:15 | 9.126 |  | 33.9 | 65.7 |  |
|  | 6/19 | 6:46 | 8.91 |  | 36.2 | 44.6 |  |
|  | 6/20 | 8:59 | 8.517 |  | 41 | 36.3 |  |
|  | 6/20 | 16:15 | 8.421 |  | 41.8 | 37.3 |  |
|  | 6/23 | 9:00 | 8.322 |  | 27.5 | 55.9 |  |
|  |  | Weight Loss = | 1.858 |  |  |  |  |
| Experimental 5 | 6/23 | 14:16 | 9.918 | <1 | 28.8 | 71.8 | excellent nice |
|  | 6/23 | 15:26 | 9.129 |  | 31.9 | 69.4 | color/shiny/clear |
|  | 6/23 | 17:19 | 8.895 |  | 32.8 | 64.4 |  |
|  | 6/24 | 8:50 | 8.488 |  | 33.5 | 62.3 |  |
|  | 6/24 | 11:03 | 8.456 |  | 35.3 | 58.5 |  |
|  | 6/24 | 14:31 | 8.42 |  | 35.8 | 61.7 |  |
|  | 6/24 | 16:53 | 8.379 |  | 38.2 | 52 |  |
|  | 6/25 | 8:45 | 8.224 |  | 39.1 | 48 |  |
|  | 6/25 | 11:40 | 8.196 |  | 41.2 | 42.5 |  |
|  | 6/25 | 13:04 | 8.192 |  | 34 | 50.3 |  |
|  | 6/25 | 14:16 | 8.185 |  | 31.9 | 46.1 |  |
|  |  | Weight Loss = | 1.933 |  |  |  |  |
| Experimental 6 | 6/25 | 15:26 | 10.077 | fluidized | 28 | 75.4 | Fluidized not helpful |
|  | 6/25 | 16:44 | 9.203 |  | 28 | 71 | dull case hardened |
|  | 6/26 | 8:54 | 8.708 |  | 24.2 | 79.6 |  |
|  | 6/26 | 11:05 | 8.659 |  | 33.9 | 45 |  |
|  | 6/26 | 15:33 | 8.639 |  | 34.7 | 53.3 |  |
|  | 6/27 | 8:47 | 8.414 |  | 36.6 | 51 |  |
|  | 6/27 | 14:35 | 8.349 |  | 28 | 49 |  |
|  | 6/27 | 16:14 | 8.745 |  | 22.3 | 51.7 |  |
|  |  | Weight Loss = | 1.682 |  |  |  |  |

The results from this Example showed that by monitoring weight loss and known equilibrium relative humidity of a product, use of an ever increasing temperature ramp was seen to reduce drying cycle time by up to 80% from 10-days to 2-days. Humidity control is needed to preserve the quality of the dried capsules. Without humidity control, capsules were dented and off-color. With humidity control, capsules came out clear, shiny, and had good color, indicating that temperature and humidity control significantly improves drying cycle time while maintaining the quality of capsules.

Example 3

Use of a Control System in a Tunnel Dryer

An embodiment of the present invention was tested using standard tunnel drying equipment. A recirculation fan of equal airflow to the existing HVAC system was added to drying tunnels used for drying softgel capsules. The drying system includes temperature sensors, humidity sensors, flow sensors, heating elements, and a damper valve to control the supply of dry cool air into the drying tunnel, as shown in FIG. 7 and as discussed above. A recirculation fan increases the airflow. A heating element increases the temperature within the tunnel. A flow control valve is used to influence the relative humidity in the tunnel by restricting the flow of dry air from the HVAC system into the recirculation loop. Moisture evaporating from the capsules provided humidity in the drying tunnel. The differential relative humidity was monitored by humidity sensors located before and after the tunnel and was maintained by the flow control valve, which was used to allow incremental amounts of dry air from the HVAC system into the tunnel. In this particular design, the velocity of air into the tunnel could be reduced, which subsequently increased the relative humidity as the effects of evaporative cooling lessened.

Air Handling Test

The HVAC air handler regulated flow based on the summation of the airflow required by each tunnel. This was meant to conserve energy when the tunnels are not needed. The maximum airflow through the air handler is 3500 m$^3$/hr. Based on the manufacturer's recommendation, the maximum duct pressure is 1200 Pa. To avoid damage to the duct, interlocks were installed to open a bypass damper at 960 Pa, and shut down the air handler at 1080 Pa.

With all dampers, valves, and bypasses closed, the minimum airflow recorded was 1200 m$^3$/hr. The minimum airflow recorded through each tunnel was 220 m$^3$/hr, 260 m$^3$/hr, and 300 m$^3$/hr, respectively. As a result, an estimated 420 m$^3$/hr of airflow was leaked through the bypass damper, a loss of 35%.

With the HVAC at 100%, the maximum airflow through each modified tunnel was individually measured at 2221 m$^3$/hr, 2116 m$^3$/hr, and 2201 m$^3$/hr, respectively. With each tunnel set in AUTO for 850 m$^3$/hr, it was found that a 30% correction factor needed to be added to the HVAC set point in order to maintain enough pressure to get the required airflow. This may be explained by the leakage of air through the bypass damper.

For the recirculated air flow, with the recirculation fans off, the minimum airflow through the recirculation ducts was 18 m$^3$/hr, 20 m$^3$/hr and 46 m$^3$/hr, respectively. This should be considered as zero, as a check valve is installed between the recirculation fan and HVAC. To avoid damaging the motor, a minimum frequency of 6 Hz was set on the Variable frequency Drive (VFD). Following this advice, the minimum frequency of the Air Handler was also set to 6 Hz. Due to the weight of the check valve, the recirculated airflow did not increase until the fan speed reached 30-40 Hz. This represents an airflow of 260-290 m$^3$/hr. As a result, some control may have been lost toward the end of drying.

With the recirculation fans at 100%, and HVAC airflow into the tunnel set for 850 m$^3$/hr in AUTO, the maximum recirculated airflow in the tunnels was 1685 m³/hr, 2067 m³/hr, and 1705 m³/hr, respectively. The difference is due to a delicate balance of pressure between the HVAC and recirculation fan. The specification for the recirculation fan was 2400 m³/hr. Therefore, the recirculation fans failed to meet specifications. For subsequent tests, the maximum frequency of the recirculation fans was temporarily set to 77 Hz.

Humidity Control

The airflow was controlled in cascade by the differential relative humidity controller at a set point of 25% dRH. The differential relative humidity was maintained at 25% dRH and the minimum relative humidity was 15% RH using the algorithm:

$$=IF(RH1>\text{Min},(IF(RH2<(\text{DIFF}+\text{DIFF}),(RH2-\text{MIN}),\text{DIFF}),(RH2-\text{MIN}))$$

The differential relative humidity was recalculated to ensure RH1 did not drop below the 15% RH minimum.

Temperature Control

The maximum temperature was limited by a 40° C. sensor. With the temperature set for 35° C. in AUTO, it was found that the control valve did not open until ~30% and did not close until ~20%, making temperature control more difficult.

Results

During the analysis, there were several instances where airflows did not reach expectations because the recirculation fans failed to meet specifications. A correction factor had to be added to the HVAC set point because the sum of the tunnel airflows did not add-up. This was likely due to leakage through the bypass damper. Additionally, the airflow seemed to be limited due to pressure drop. The average airflow at the return vent above the door measured 1964 m³/hr.

Figure 11:
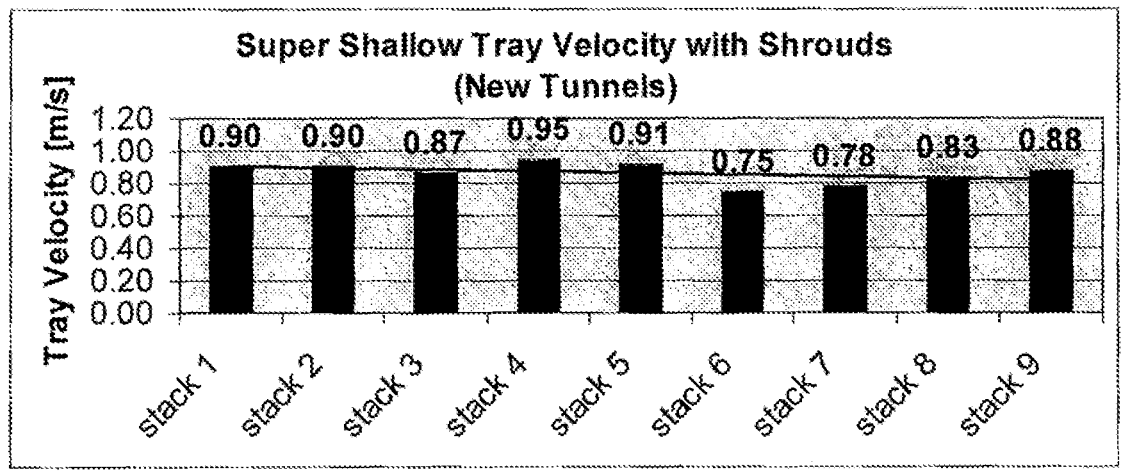
FIG. 11 shows graphs of the air velocity around the stacks in a tunnel dryer.
Figure 11:
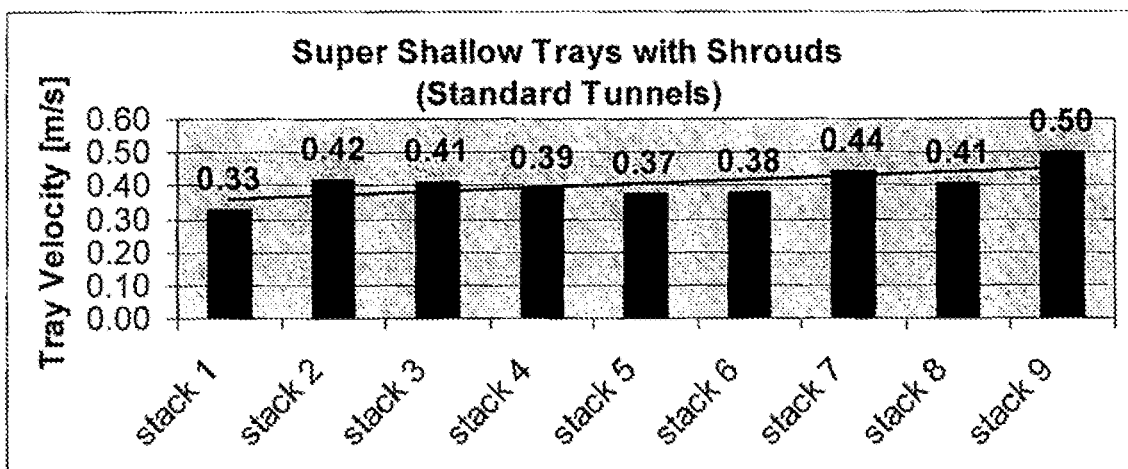
Figure 11:
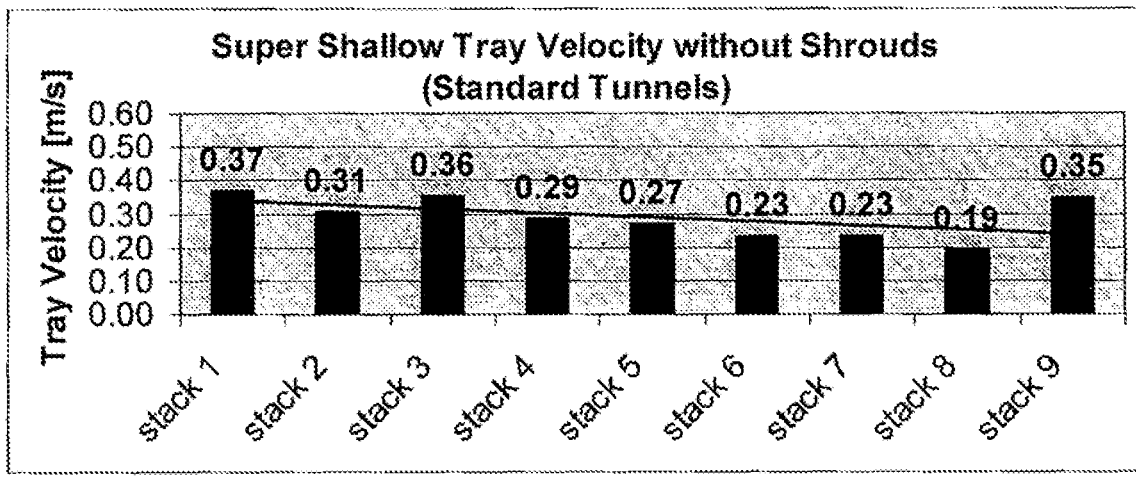

Using the measured average airflow of 1964 m³/hr described above, the velocity of airflow across the trays was measured with shrouds placed in between each stack. The shrouds were plastic inserts placed between each stack to prevent airflow from going around the stack and redirect airflow to go through the stack. The results showed a high and steady velocity between the trays. However, the air velocity was far less than the 1.53 m/s specified. The shrouds were relatively worn and some were cracked. Therefore, a different shroud design may be needed. Consequently, better velocity potentially could have been achieved. Despite lower than expected air flow, tray velocities did show an improvement over past measurements. A comparison of the results for the airflow velocities is shown in FIG. 11.

The airflow in standard tunnels without shrouds averaged 0.29 m/s. The airflow in standard tunnels with shrouds averaged 0.41 m/s, and the airflow in the modified tunnels with shrouds averaged 0.86 m/s. Therefore, airflow in the modified tunnels with shrouds is more than twice that of standard tunnels with shrouds, and nearly three times that of standard tunnels without shrouds.

The tray gap area of super shallow stacks in the tunnel measured 5360 cm². The velocity of air through, above, to the sides, and below the stacks in the modified tunnels averaged 0.69 m/s. As a result, the airflow through the stacks in the tunnel measured 1330 m³/hr, with the expected airflow being 1964 m³/hr. This was a discrepancy of 32%.

Wet Test

Approximately 15 kg of water was loaded onto each stack (~180 ml/tray) to simulate the amount of water evaporated from softgel capsules in a drying tunnel. The control system immediately picked up the humidity and lower temperature coming off the first stack as soon as the stack entered the tunnel. The recirculation fan immediately turned on to full speed as it saw a >1° C. differential temperature. After 2-3 hours, all 9 stacks with water had been placed in the tunnel. Both temperature and humidity sensors recorded each stack as they entered the tunnel.

The evaporation of water was excessive and the relative humidity after about 4 hours reached 91% RH. As the relative humidity increased, the airflow control valve closed in order to maintain a differential relative humidity of 25% dRH.

To increase the speed of the test, the temperature was ramped up to 34° C. after 3 hours. The hot water valve opened and then closed to maintain this set point. Despite the supply temperature reaching 34° C., the return temperature barely achieved 28° C. before the process began to cool. This indicates that the last stack still contained some moisture, but continued to dry at safe temperatures. Additionally, the return temperature due to evaporative cooling never fell below 18° C., whereas the wet-bulb temperature is typically 9° C. As a result, the capsules were kept warm and were expected to dry faster. Toward the end of drying, the return relative humidity dropped below 35% RH, which is an indicator that the drying process was almost complete and the temperature began to return to normal at 24° C.

Once the differential temperature dropped below 1° C., the recirculation fan slowed down. As the recirculation fan slowed down, the relative humidity increased, and the airflow controller opened to draw down the relative humidity. The airflow controller closed as the minimum humidity set-point of 15% RH was reached. Eventually, all three of recirculation, temperature and humidity control slow to a stop and the drying process was complete. The trays were inspected and no water remained on the stacks. The process started and stopped automatically.

Despite the airflow failing to meet specifications, the control scheme was able to start and stop the dryer automatically.

Example 4

Figure 12:
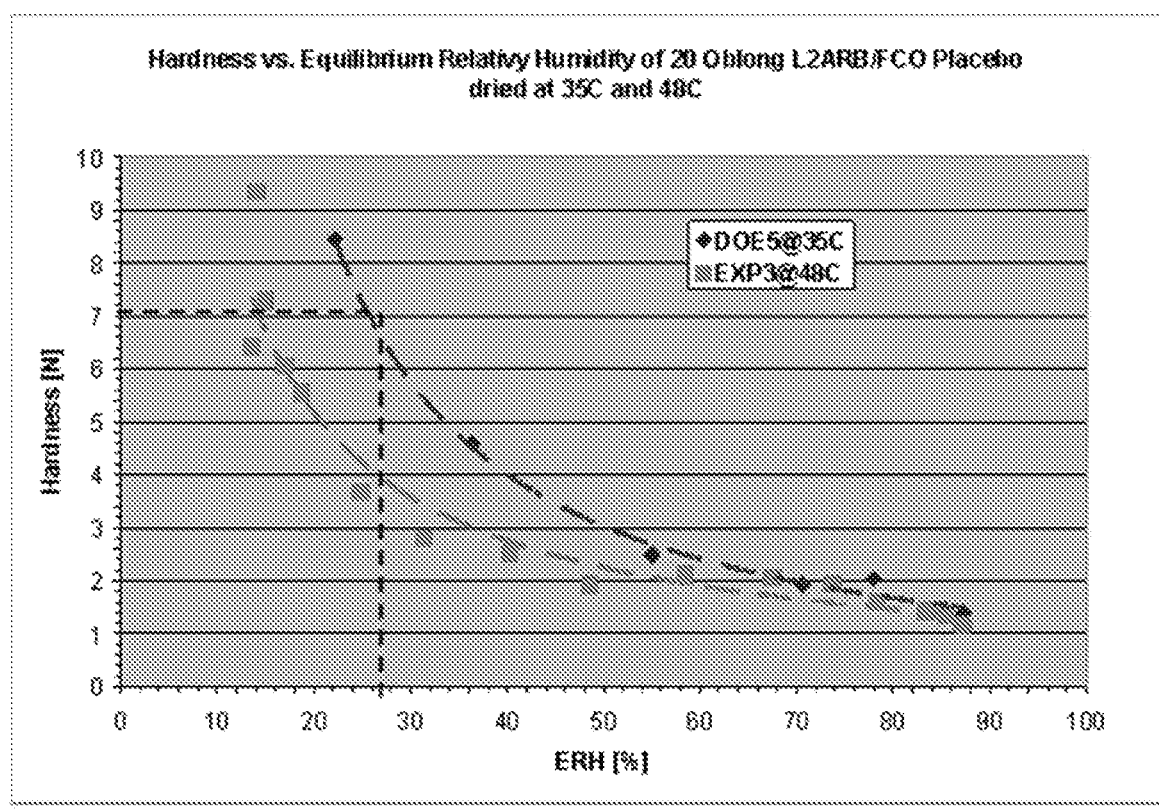
FIG. 12 is a graph showing the hardness's of placebo capsules versus equilibrium relative humidity when dried at two different temperatures.

Placebo capsules made from L2ARB standard gelatin and fractionated coconut oil (FCO) were produced using standard manufacturing processes and dried at two different elevated temperatures of 35° C. and 48° C. The hardness of the capsules was measured over a range of ERHs using a Bareiss Digitest Gelomat. The results are shown in FIG. 12. The heat treated capsules are softer at similar relative humidities, and are less brittle and less likely to leak.

It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meanings of the terms in which the appended claims are expressed.

What is claimed is:

1. A method of drying soft capsules comprising steps of:
   a) supplying an airflow to said soft capsules at a velocity of the air across the soft capsules of from about 0.15 m/s to about 13 m/s;
   b) increasing, over time, a drying temperature to which said soft capsules are exposed while ensuring that the drying temperature remains below a melting temperature of a capsule shell of the soft capsules;

c) exposing said soft capsules to an initial relative humidity of from about 49% RH to about 79% RH;
d) decreasing the relative humidity to which the soft capsules are exposed as the capsules dry until an equilibrium relative humidity of the soft capsules reaches a desired relative humidity; and
e) exposing the soft capsules from step d) to a temperature of from 20-25° C.

2. The method of claim 1 further comprising a step of:
decreasing the velocity of the airflow to which the soft capsules are exposed, as the soft capsules dry.

3. The method of claim 1, wherein the relative humidity is controlled so that a differential between the relative humidity to which the soft capsules are exposed and the equilibrium relative humidity of the soft capsules is maintained at about 15% dRH to about 35% dRH.

4. The method of claim 1, wherein the soft capsules are lipophilic.

5. The method of claim 4, wherein the initial relative humidity is from about 49% RH to about 79% RH.

6. The method of claim 1, wherein a lowest relative humidity to which the soft capsules are exposed is from about 10% RH to about 24% RH.

7. The method of claim 1, wherein the soft capsules are hydrophilic.

8. The method of claim 7, wherein the wherein the initial relative humidity is from about 49% RH to about 79% RH and a lowest relative humidity to which the soft capsules are exposed is from about 23% RH to about 57% RH.

9. A drying system for drying soft capsules comprising:
at least one dryer;
a unit in fluid communication with the dryer to provide an airflow to the dryer;
a humidifier configured to be able to increase a relative humidity within the dryer;
a heater configured to be able to increase a temperature of air in the dryer; and
a flow control valve configured to control an amount of the airflow from the unit to the dryer;
wherein the heater is configured to increase the temperature over time according to a temperature ramp based on a melting point of a capsule shell of the soft capsules and a combination of the flow control valve and the humidifier is configured to control the relative humidity in the dryer such that the relative humidity in the dryer decreases over time from an initial relative humidity of 49% RH to 79% RH to an endpoint relative humidity of 10% RH to 24% RH, and the relative humidity is decreased in a manner whereby a differential between the relative humidity in the dryer and the equilibrium relative humidity of the soft capsules is maintained at 15% dRH to 35% dRH.

10. The drying system of claim 9, further comprising a recirculation fan located and configured to recirculate a return air stream from an exhaust of the dryer to the unit that provides the airflow to the dryer.

11. The drying system of claim 10, wherein the humidifier comprises the recirculation fan.

12. The drying system of claim 9, further comprising a recirculation fan located and configured to recirculate a return air stream from an exhaust of the dryer to the unit that provides the airflow to the dryer, and wherein the flow control valve is configured such that reducing the amount of airflow from the unit to the dryer increases the relative humidity within the dryer and increasing the amount of airflow from the unit to the dryer decreases the relative humidity within the dryer.

13. The drying system of claim 9, wherein a combination of the flow control valve and the humidifier is configured to control the relative humidity in the dryer such that the relative humidity in the dryer decreases over time from an initial relative humidity of about 49% RH to about 79% RH to an endpoint relative humidity of about 23% RH and about 57% RH.

14. A method of drying soft capsules, said method comprising steps of:
a) supplying a flow of air to said capsules at a velocity of the air across the soft capsules of from about 0.15 m/s to about 13 m/s;
b) increasing, over time, a drying temperature to which said soft capsules are exposed while ensuring that the drying temperature remains below a melting temperature of a capsule shell;
c) maintaining a differential between a relative humidity in a dryer and an equilibrium relative humidity of the soft capsules of about 15% dRH to about 35% dRH until the equilibrium relative humidity of the soft capsules reaches a desired relative humidity; and
d) exposing the soft capsules from step c) to a temperature of from 20-25° C.

* * * * *

UNITED STATES PATENT AND TRADEMARK OFFICE
CERTIFICATE OF CORRECTION

| | | |
|---|---|---|
| PATENT NO. | : 11,026,865 B2 | Page 1 of 1 |
| APPLICATION NO. | : 16/467436 | |
| DATED | : June 8, 2021 | |
| INVENTOR(S) | : Hart et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 134 days.

Signed and Sealed this
Seventh Day of February, 2023

Katherine Kelly Vidal
*Director of the United States Patent and Trademark Office*